US012605150B2

(12) United States Patent
Cohn et al.

(10) Patent No.: US 12,605,150 B2
(45) Date of Patent: Apr. 21, 2026

(54) SYSTEMS, DEVICES, AND METHODS FOR CORING TISSUE

(71) Applicant: Prana Thoracic, Inc., Houston, TX (US)

(72) Inventors: William Cohn, Bellaire, TX (US); Terry Daglow, Houston, TX (US); Matthew Kuhn, Houston, TX (US); Jonathan Melchor, Warwick, RI (US); Theodore Mick, Houston, TX (US); Chris Mills, Houston, TX (US); Steven Nguyen, Cypress, TX (US); Jorge Salazar, New York, NY (US)

(73) Assignee: Prana Thoracic, Inc., Houston, TX (US)

( * ) Notice: Subject to any disclaimer, the term of this patent is extended or adjusted under 35 U.S.C. 154(b) by 886 days.

(21) Appl. No.: 17/226,738

(22) Filed: Apr. 9, 2021

(65) Prior Publication Data

US 2021/0219967 A1     Jul. 22, 2021

Related U.S. Application Data

(63) Continuation-in-part of application No. 16/512,628, filed on Jul. 16, 2019, now Pat. No. 11,723,708, and
(Continued)

(51) Int. Cl.
| | |
|---|---|
| *A61B 18/14* | (2006.01) |
| *A61B 10/02* | (2006.01) |
| *A61B 17/32* | (2006.01) |

(52) U.S. Cl.
CPC .. *A61B 10/0233* (2013.01); *A61B 17/320092* (2013.01); *A61B 2017/320044* (2013.01); *A61B 2017/320095* (2017.08)

(58) Field of Classification Search
CPC .............. A61B 18/085; A61B 18/1477; A61B 18/1482; A61B 18/1815; A61B 18/1442;
(Continued)

(56) References Cited

U.S. PATENT DOCUMENTS

| | | |
|---|---|---|
| 4,007,732 A | 2/1977 | Kvavle et al. |
| 4,735,194 A | 4/1988 | Stiegmann |

(Continued)

FOREIGN PATENT DOCUMENTS

| | | |
|---|---|---|
| CN | 1221603 A | 7/1999 |
| CN | 102656171 A | 9/2012 |

(Continued)

OTHER PUBLICATIONS

Extended European Search Report for European Application No. EP19189128 dated Oct. 9, 2019, 4 pages.
(Continued)

*Primary Examiner* — Thomas A Giuliani

(57) ABSTRACT

A method for removing tissues may comprise disposing a tissue resection device at a target tissue site, causing the tissue resection device to resect a core of tissue from the target tissue site, removing the core of tissue from the body, wherein the removing the core of tissue from the body creates a core cavity at the target tissue site.

31 Claims, 6 Drawing Sheets

Related U.S. Application Data a continuation-in-part of application No. 16/512,616, filed on Jul. 16, 2019, now abandoned.

(60) Provisional application No. 63/017,724, filed on Apr. 30, 2020.

(58) Field of Classification Search
CPC .......... A61B 2018/00607; A61B 2018/00589; A61B 2018/00601; A61B 2018/142; A61B 2018/0063; A61B 2018/1425; A61B 2018/126; A61B 2018/1435; A61B 2018/1407; A61B 2018/141; A61B 2018/1412; A61B 2018/1452; A61B 2018/1455; A61B 2018/145; A61B 10/0233; A61B 10/0266; A61B 17/320092; A61B 17/3209; A61B 17/320016; A61B 17/32053; A61B 17/12013; A61B 17/32093; A61B 2017/320095; A61B 2017/320064; A61B 2017/320052
USPC ..... 600/567; 606/41, 45, 46, 48–52; 607/98, 607/99, 101, 113, 115, 116
See application file for complete search history.

(56) References Cited

U.S. PATENT DOCUMENTS

| | | | |
|---|---|---|---|
| 5,103,804 A | | 4/1992 | Abele et al. |
| 5,133,360 A | * | 7/1992 | Spears ............... A61B 10/0266 |
| | | | 600/567 |
| 5,190,561 A | | 3/1993 | Graber |
| 5,196,024 A | | 3/1993 | Barath |
| 5,353,804 A | | 10/1994 | Kornberg et al. |
| 5,507,743 A | | 4/1996 | Edwards et al. |
| 5,643,282 A | | 7/1997 | Kieturakis |
| 5,651,788 A | | 7/1997 | Fleischer et al. |
| 5,681,281 A | | 10/1997 | Vigil et al. |
| 5,779,698 A | | 7/1998 | Clayman et al. |
| 5,810,811 A | | 9/1998 | Yates et al. |
| 5,843,108 A | | 12/1998 | Samuels |
| 5,882,316 A | | 3/1999 | Chu et al. |
| 5,908,435 A | | 6/1999 | Samuels |
| 5,928,163 A | | 7/1999 | Roberts et al. |
| 5,961,526 A | | 10/1999 | Chu et al. |
| 6,022,362 A | | 2/2000 | Lee et al. |
| 6,213,957 B1 | | 4/2001 | Milliman et al. |
| 6,258,108 B1 | | 7/2001 | Lary |
| 6,493,589 B1 | | 12/2002 | Medhkour et al. |
| 6,574,513 B1 | | 6/2003 | Collura et al. |
| 6,652,520 B2 | | 11/2003 | Moorman et al. |
| 6,770,070 B1 | | 8/2004 | Balbierz |
| 6,974,467 B1 | | 12/2005 | Gonzales, Jr. |
| 7,517,352 B2 | | 4/2009 | Evans et al. |
| 7,582,055 B2 | * | 9/2009 | Komiya ................. A61B 17/29 |
| | | | 600/106 |
| 7,811,303 B2 | | 10/2010 | Fallin et al. |
| 8,239,030 B1 | | 8/2012 | Hagedorn et al. |
| 8,506,503 B2 | | 8/2013 | Fritscher-Ravens et al. |
| 8,602,973 B2 | | 12/2013 | Wendlandt |
| 8,734,362 B2 | | 5/2014 | Boyle, Jr. |
| 9,241,692 B2 | * | 1/2016 | Gunday ................. A61B 10/04 |
| 9,521,961 B2 | * | 12/2016 | Silverstein ............. A61B 8/463 |
| 9,895,190 B2 | | 2/2018 | Trieu |
| 10,022,179 B2 | | 7/2018 | Feinberg et al. |
| 10,039,529 B2 | | 8/2018 | Kerr et al. |
| 10,130,369 B2 | | 11/2018 | Fung et al. |
| 10,314,578 B2 | | 6/2019 | Leimbach et al. |
| 10,413,368 B2 | | 9/2019 | Nilsagard et al. |
| 10,555,769 B2 | | 2/2020 | Worrell et al. |
| 10,595,835 B2 | | 3/2020 | Kerr et al. |
| 11,103,272 B2 | | 8/2021 | Boyle et al. |
| 11,331,087 B2 | | 5/2022 | Boyle, Jr. |
| 11,723,708 B2 | * | 8/2023 | Cohn ................... A61B 18/082 |
| | | | 600/566 |
| 12,102,372 B2 | | 10/2024 | Cohn et al. |
| 2002/0019597 A1 | | 2/2002 | Dubrul et al. |
| 2002/0049442 A1 | * | 4/2002 | Roberts ............. A61B 18/1445 |
| | | | 606/50 |
| 2002/0059938 A1 | | 5/2002 | Fogarty et al. |
| 2002/0082614 A1 | | 6/2002 | Logan et al. |
| 2002/0095101 A1 | | 7/2002 | Fontenot |
| 2002/0095152 A1 | | 7/2002 | Ciarrocca et al. |
| 2002/0115997 A1 | | 8/2002 | Truckai et al. |
| 2003/0114911 A1 | | 6/2003 | Lupton |
| 2003/0129382 A1 | | 7/2003 | Treat |
| 2003/0233099 A1 | | 12/2003 | Danaek et al. |
| 2004/0010206 A1 | | 1/2004 | Dubrul et al. |
| 2004/0122349 A1 | | 6/2004 | Lafontaine et al. |
| 2004/0133254 A1 | | 7/2004 | Sterzer et al. |
| 2004/0147917 A1 | | 7/2004 | Mueller et al. |
| 2004/0215296 A1 | | 10/2004 | Ganz et al. |
| 2004/0254572 A1 | | 12/2004 | McIntyre et al. |
| 2005/0113854 A1 | | 5/2005 | Uckele |
| 2005/0288695 A1 | | 12/2005 | Jenson et al. |
| 2006/0009756 A1 | | 1/2006 | Francischelli et al. |
| 2006/0025815 A1 | | 2/2006 | McGurk et al. |
| 2006/0069388 A1 | | 3/2006 | Truckai et al. |
| 2006/0074484 A1 | | 4/2006 | Huber |
| 2006/0190037 A1 | | 8/2006 | Ginn et al. |
| 2007/0005084 A1 | | 1/2007 | Clague et al. |
| 2007/0015984 A1 | | 1/2007 | Yeo et al. |
| 2007/0043350 A1 | | 2/2007 | Soltesz et al. |
| 2007/0073343 A1 | | 3/2007 | Jahns et al. |
| 2007/0123852 A1 | | 5/2007 | Deem et al. |
| 2007/0156156 A1 | | 7/2007 | Badie |
| 2007/0179494 A1 | | 8/2007 | Faure |
| 2007/0249911 A1 | | 10/2007 | Simon |
| 2007/0265491 A1 | | 11/2007 | Krag et al. |
| 2008/0108950 A1 | | 5/2008 | Rioux et al. |
| 2008/0110457 A1 | | 5/2008 | Barry et al. |
| 2009/0054805 A1 | | 2/2009 | Boyle, Jr. |
| 2009/0105745 A1 | | 4/2009 | Culbert |
| 2010/0036312 A1 | | 2/2010 | Krolik et al. |
| 2010/0069919 A1 | | 3/2010 | Carls et al. |
| 2010/0168821 A1 | | 7/2010 | Johnson et al. |
| 2010/0174306 A1 | * | 7/2010 | Mitelberg ...... A61B 17/320783 |
| | | | 606/190 |
| 2010/0191279 A1 | | 7/2010 | Kassab et al. |
| 2010/0274238 A1 | | 10/2010 | Klimovitch |
| 2010/0312141 A1 | * | 12/2010 | Keast ....................... A61B 8/12 |
| | | | 600/567 |
| 2011/0105841 A1 | | 5/2011 | Kutikov et al. |
| 2011/0105947 A1 | * | 5/2011 | Fritscher-Ravens ... A61B 10/04 |
| | | | 600/567 |
| 2011/0190764 A1 | | 8/2011 | Long et al. |
| 2012/0053566 A1 | | 3/2012 | Tada et al. |
| 2012/0071866 A1 | | 3/2012 | Kerr et al. |
| 2012/0071922 A1 | | 3/2012 | Shanley et al. |
| 2012/0109174 A1 | | 5/2012 | Vetter |
| 2012/0143020 A1 | | 6/2012 | Bordoley et al. |
| 2012/0253229 A1 | | 10/2012 | Cage |
| 2012/0289776 A1 | | 11/2012 | Keast et al. |
| 2012/0316608 A1 | | 12/2012 | Foley |
| 2013/0018414 A1 | | 1/2013 | Widomski et al. |
| 2013/0031735 A1 | | 2/2013 | Brand et al. |
| 2013/0046140 A1 | | 2/2013 | Pravong et al. |
| 2013/0150701 A1 | | 6/2013 | Budar et al. |
| 2013/0190809 A1 | | 7/2013 | Vidlund et al. |
| 2013/0197357 A1 | | 8/2013 | Green et al. |
| 2014/0236184 A1 | | 8/2014 | Leimbach et al. |
| 2014/0257359 A1 | | 9/2014 | Tegels et al. |
| 2014/0275979 A1 | | 9/2014 | Fujimoto et al. |
| 2014/0276009 A1 | | 9/2014 | Boyle, Jr. |
| 2014/0276687 A1 | | 9/2014 | Goodman et al. |
| 2014/0276732 A1 | | 9/2014 | Strobl et al. |
| 2014/0276911 A1 | | 9/2014 | Smith et al. |
| 2014/0277039 A1 | | 9/2014 | Liberatore et al. |
| 2014/0277071 A1 | | 9/2014 | Wu et al. |
| 2014/0343348 A1 | | 11/2014 | Kaplan et al. |
| 2015/0057570 A1 | * | 2/2015 | Chin ....................... A61B 90/11 |
| | | | 606/46 |

(56) References Cited

U.S. PATENT DOCUMENTS

| | | |
|---|---|---|
| 2015/0112225 A1 | 4/2015 | Prow et al. |
| 2015/0141981 A1 | 5/2015 | Price et al. |
| 2015/0265331 A1 | 9/2015 | Fleury et al. |
| 2015/0282823 A1 | 10/2015 | Trees et al. |
| 2015/0342638 A1 | 12/2015 | Smith et al. |
| 2016/0067465 A1 | 3/2016 | Gerrans et al. |
| 2016/0192911 A1 | 7/2016 | Kassab et al. |
| 2016/0192999 A1 | 7/2016 | Stulen et al. |
| 2016/0206366 A1 | 7/2016 | Clauda et al. |
| 2016/0220294 A1 | 8/2016 | Babkin et al. |
| 2016/0367279 A1 | 12/2016 | Orphanos et al. |
| 2017/0000553 A1 | 1/2017 | Wiener et al. |
| 2017/0000554 A1 | 1/2017 | Yates et al. |
| 2017/0042516 A1 | 2/2017 | Boyle, Jr. |
| 2017/0202595 A1 | 7/2017 | Shelton, IV |
| 2017/0281214 A1 | 10/2017 | Brown et al. |
| 2018/0140319 A1* | 5/2018 | Saidi ................. A61B 17/1615 |
| 2018/0153604 A1 | 6/2018 | Ayvazyan et al. |
| 2018/0193060 A1 | 7/2018 | Reddy et al. |
| 2018/0235650 A1 | 8/2018 | Beaupre |
| 2019/0000534 A1 | 1/2019 | Messerly et al. |
| 2019/0038306 A1 | 2/2019 | Lindner et al. |
| 2019/0076164 A1 | 3/2019 | Boyle, Jr. et al. |
| 2019/0099197 A1 | 4/2019 | Boyle, Jr. et al. |
| 2019/0201029 A1 | 7/2019 | Shelton, IV et al. |
| 2019/0246946 A1 | 8/2019 | Kopel et al. |
| 2019/0269387 A1 | 9/2019 | Kerr |
| 2019/0388132 A1 | 12/2019 | Azamian et al. |
| 2020/0038089 A1 | 2/2020 | Cohn et al. |
| 2020/0038090 A1 | 2/2020 | Cohn et al. |
| 2020/0038097 A1 | 2/2020 | Cohn et al. |
| 2020/0390427 A1 | 12/2020 | Eisenthal et al. |
| 2021/0322091 A1 | 10/2021 | Addison et al. |
| 2021/0338215 A1 | 11/2021 | Cohn et al. |
| 2021/0338218 A1 | 11/2021 | Cohn et al. |
| 2021/0338265 A1 | 11/2021 | Cohn et al. |
| 2021/0338315 A1 | 11/2021 | Cohn et al. |
| 2021/0338316 A1 | 11/2021 | Cohn et al. |
| 2021/0378731 A1 | 12/2021 | Boateng et al. |
| 2021/0393332 A1 | 12/2021 | Cohn et al. |
| 2022/0031382 A1 | 2/2022 | Cohn et al. |
| 2022/0047314 A1 | 2/2022 | Cohn et al. |
| 2022/0047322 A1 | 2/2022 | Cohn et al. |
| 2022/0225970 A1 | 7/2022 | Boyle, Jr. |
| 2023/0380878 A1 | 11/2023 | Cohn et al. |
| 2025/0228599 A1 | 7/2025 | Cohn et al. |

FOREIGN PATENT DOCUMENTS

| | | |
|---|---|---|
| DE | 102016101915 A1 | 8/2017 |
| EP | 1340469 A1 | 9/2003 |
| EP | 2866700 A1 | 5/2015 |
| EP | 3603546 A1 | 2/2020 |
| JP | H11244298 A | 9/1999 |
| JP | 3287788 B2 | 6/2002 |
| JP | 2003516800 A | 5/2003 |
| JP | 2004230054 A | 8/2004 |
| JP | 2004528056 A | 9/2004 |
| JP | 2007185495 A | 7/2007 |
| JP | 2008538518 A | 10/2008 |
| JP | 2009536083 A | 10/2009 |
| JP | 2012500098 A | 1/2012 |
| JP | 2012183302 A | 9/2012 |
| JP | 2013509255 A | 3/2013 |
| JP | 2014030555 A | 2/2014 |
| JP | 2014113211 A | 6/2014 |
| JP | 2018118115 A | 8/2018 |
| JP | 2019505320 A | 2/2019 |
| JP | 2020018853 A | 2/2020 |
| JP | 2020506772 A | 3/2020 |
| WO | WO-9603163 A1 | 2/1996 |
| WO | WO-2005110508 A2 | 11/2005 |
| WO | WO-2006108067 A2 | 10/2006 |
| WO | WO-2007014313 A2 | 2/2007 |
| WO | WO-2010001405 A1 | 1/2010 |
| WO | WO-2011053648 A1 | 5/2011 |
| WO | WO-2011094110 A1 | 8/2011 |
| WO | WO-2014172396 A2 | 10/2014 |
| WO | WO-2018144898 A1 | 8/2018 |
| WO | WO-2018218210 A1 | 11/2018 |
| WO | WO-2019130110 A1 | 7/2019 |
| WO | WO-2019239338 A2 | 12/2019 |
| WO | WO-2020006660 A1 | 1/2020 |
| WO | WO-2021220220 A1 | 11/2021 |
| WO | WO-2021220221 A2 | 11/2021 |
| WO | WO-2021220222 A2 | 11/2021 |
| WO | WO-2021220223 A1 | 11/2021 |
| WO | WO-2021220224 A2 | 11/2021 |
| WO | WO-2021220225 A1 | 11/2021 |
| WO | WO-2021250526 A1 | 12/2021 |
| WO | WO-2021260468 A1 | 12/2021 |
| WO | WO-2022023998 A1 | 2/2022 |
| WO | WO-2022034412 A1 | 2/2022 |
| WO | WO-2022038433 A1 | 2/2022 |
| WO | WO-2022214896 A1 | 10/2022 |

OTHER PUBLICATIONS

Extended European Search Report for European Application No. EP19189139 dated Oct. 9, 2019, 7 pages.

Final office action for U.S. Appl. No. 16/512,649, mailed Jan. 20, 2023, 10 pages.

Final office action for U.S. Appl. No. 16/512,649, mailed Mar. 14, 2022, 10 pages.

Indian Office Action for Indian Application No. IN201914029519 dated Sep. 23, 2022, 9 pages.

Indian Office Action for Indian Patent Application No. IN201914029517 dated Sep. 27, 2022, 8 pages.

Indian Office Action for Indian Patent Application No. IN201914029518 dated Oct. 28, 2022, 5 pages.

International Search Report and Written Opinion for Application No. PCT/IB2021/053588, mailed Jul. 1, 2021, 11 pages.

International Search Report and Written Opinion for Application No. PCT/IB2022/052603, mailed Jun. 10, 2021, 12 pages.

Japanese Office Action for Japanese Application No. JP2019139537 dated Jun. 6, 2023, 3 pages.

Non final office action for U.S. Appl. No. 16/512,616, mailed Dec. 15, 2022, 10 pages.

Non final office action for U.S. Appl. No. 16/512,649, mailed Jul. 25, 2022, 11 pages.

Non final office action for U.S. Appl. No. 16/512,649, mailed Sep. 21, 2021, 10 pages.

Non-Final Office Action for U.S. Appl. No. 18/335,975 dated Oct. 23, 2023, 17 pages.

Non-Final Office Action for U.S. Appl. No. 16/512,628 dated Sep. 22, 2022, 7 pages.

Office Action for Brazilian Application No. BR102019015643 mailed Dec. 26, 2023, 5 pages.

Office Action for Japanese Application No. JP20190139478 dated Nov. 21, 2023, 9 pages.

Office Action for Japanese Application No. JP2019139478 dated May 21, 2023, 5 pages.

Notice of Allowance for U.S. Appl. No. 18/335,975 dated May 8, 2024, 8 pages.

Notice of Allowance for U.S. Appl. No. 18/335,975 mailed Jul. 31, 2024, 8 pages.

Restriction Requirement for U.S. Appl. No. 17/226,738 mailed Feb. 13, 2024, 7 pages.

Bhamidipati., et al., "BioGlue in 2011: What is its Role in Cardiac Surgery?" The Journal of ExtraCorporeal Technology, JECT. 2012; 44:P6-P12.

Notice of Reasons for Refusal for Japanese Application No. 2024-071473 mailed Mar. 5, 2025, with English Translation, 9 pages.

Final Office Action for U.S. Appl. No. 17/319,827 dated Aug. 6, 2025, 9 pages.

BR Application No. BR102019015646-5, Office Action mailed Sep. 11, 2025, Applicant Ethicon Inc., with English translation, 5 pages.

EP Application No. 21 731 309.7, Office Action mailed Oct. 23, 2025; Applicant Prana Thoracic Inc.; 8 pages.

(56)     References Cited

OTHER PUBLICATIONS

JP Application No. 2024-071473, Notice of Allowance mailed Sep. 22, 2025; Applicant Prana Thoracic Inc., with English translation, 5 pages.

* cited by examiner

1422

1424

1420

1605          1605          1605

1510

1515          1510

1802 —

Dispose a tissue resection device at a target site

1804 —

Resect a core of tissue

1806 —

Remove the core of tissue

1808 —

Seal target site

SYSTEMS, DEVICES, AND METHODS FOR CORING TISSUE

CROSS-REFERENCE TO RELATED APPLICATIONS

This application is a continuation-in-part of U.S. patent application Ser. No. 16/512,616, filed on Jul. 16, 2019, now abandoned, and U.S. patent application Ser. No. 16/512,628, filed on Jul. 16, 2019, now U.S. Pat. No. 11,723,708, issued Aug. 15, 2023, and claims priority to and the benefit of U.S. Patent Application No. 63/017,724, filed Apr. 30, 2020, which is hereby incorporated by reference in their entirety.

BACKGROUND

Cancer is not a single disease, but rather a collection of related diseases that can start essentially anywhere in the body. Common amongst all types of cancer is that the body's cells begin to divide without stopping, proliferating and potentially spreading into surrounding tissues. In the normal course of events, cells grow and divide to form new cells as required by the body and when they become damaged or old, they die, and new cells replace the damaged or old cells; however, cancer interrupts this process. With cancer, the cells become abnormal, and cells that should die do not and new cells form when they are not needed. These new cells can reproduce or proliferate without stopping and may form growths called tumors.

Cancerous tumors are malignant, which means they can spread into or invade surrounding healthy tissue. In addition, cancer cells can break off and travel to remote areas in the body through blood or in the lymph system. Benign tumors, unlike malignant tumors, do not spread or invade surrounding tissue; however, they may grow large and cause damage. Both malignant and benign tumors may be removed or treated. Malignant tumors tend to grow back whereas benign tumors can grow back but are much less likely to do so.

Cancer is a genetic disease in that it is caused by changes in the genes that control the ways that cells function, especially in how they grow and divide. Genetic changes that cause cancer may be inherited or they may arise over an individual's lifetime as a result of errors that occur as cells divide or because of damage to DNA caused by certain environmental exposure, for example, industrial/commercial chemicals and ultraviolet light. The genetic changes that may cause cancer tend to affect three types of genes; namely proto-oncogenes which are involved in normal cell growth and division, tumor suppressor genes which are also involved in controlling cell growth and division, and DNA repair genes which, as the name implies, are involved in repairing damaged DNA.

More than one-hundred distinct types of cancer have been identified. The type of cancer may be named for the organ or tissue where the cancers arise, for example, lung cancer, or the type of cell that formed them, for example squamous cell cancer. Cancer, unfortunately, is a leading cause of death both in the United States and world-wide. According to the World Health Organization, the number of new cancer cases will rise to twenty-five (25) million per year over the next two decades.

Lung cancer is one of the most common cancers today. According to the World Cancer Report 2014 from the World Health Organization, lung cancer occurred in 14 million people and resulted in 8.8 million deaths world-wide, making it the most common cause of cancer-related death in men and the second most common cause of cancer-related death in women. Lung cancer or lung carcinoma is a malignant lung tumor that if left untreated can metastasize into neighboring tissues and organs. The majority of lung cancer is caused by long-term tobacco smoking; however, about 10 to 15 percent of lung cancer cases are not tobacco related. These non-tobacco cases are most often caused by a combination of genetic factors and exposure to certain environmental conditions, including radon gas, asbestos, second-hand tobacco smoke, other forms of air pollution, and other agents. The chance of surviving lung cancer as well as other forms of cancer depends on early detection and treatment.

Improvements in removing tissue are needed.

SUMMARY

It may be desirable to remove a core of tissue from other target tissue sites including, but not limited to, the lungs, the liver, pancreas, or gastrointestinal (GI) tract, for which managing post-coring bleeding may be desired. A core of tissue may have a prescribed (e.g., pre-defined) shape (e.g., columnar) and dimension based on a coring apparatus. Such coring apparatus may be used to core the same or substantially the same shaped tissue core in a repeatable manner. Such coring may be distinguished from other tissue removal, for example using scissors or scalpel, where the cut tissue will not have a pre-defined shape or dimensions.

A method for coring tissue may comprise disposing a tissue resection device at a target tissue site, causing the tissue resection device to resect a core of tissue from the target tissue site, and removing the core of tissue from the body, wherein the removing the core of tissue from the body creates a core cavity at the target tissue site. The core of tissue comprises at least a portion of a tissue lesion. The resecting the core of tissue from the target tissue site may comprise mechanical transection. The resecting the core of tissue from the target tissue site may comprise the delivery of radiofrequency energy. The resecting the core of tissue from the target tissue site may comprise mechanical compression and the delivery of radiofrequency energy. The resecting the core of tissue from the target tissue site may comprise transection with an energized wire. The resecting the core of tissue from the target tissue site may comprise one of more of mechanical compression, the delivery of radiofrequency energy, the delivery of microwave energy, the delivery of ultrasonic energy, or transection with an energized wire. Other resection devices and procedures may be used. The resection device may be configured for one or more of mechanical compression, the delivery of radiofrequency energy, the delivery of microwave energy, the delivery of ultrasonic energy, or transection with an energized wire.

Methods for coring tissue may further comprise inserting a sleeve into the core cavity to support a wall of the core cavity. Methods for coring tissue may further comprise delivering radiofrequency energy to at least a portion of a wall defining the core cavity. Methods for coring tissue may further comprise delivering chemotherapy to at least a portion of a wall defining the core cavity. Methods for coring tissue may further comprise delivering microwave energy to at least a portion of a wall defining the core cavity. Methods for coring tissue may further comprise delivering thermal energy to at least a portion of a wall defining the core cavity. Methods for coring tissue may further comprise delivering ultrasonic energy to at least a portion of a wall defining the core cavity.

Methods for coring tissue may further comprise sealing biological fluid vessels. The sealing biological fluid vessels may minimize flow of biological fluids into the cavity core. The sealing may be effected using at least mechanical compression. The sealing may be effected using at least radiofrequency energy. The sealing may be effected using at least microwave energy. The sealing may be effected using at least ultrasonic energy. The sealing may be effected using one or more of compression or delivery of energy such as radiofrequency, microwave, ultrasonic, or thermal energy.

The present disclosure relates to a system, device and method for performing lung lesion removal. A lung needle biopsy is typically performed when an abnormality is found on an imaging test, for example, an X-ray or CAT scan. In a lung needle biopsy, a fine needle is used to remove sample of lung tissue for examining under a microscope to determine the presence of abnormal cells. Tissue diagnosis is challenging in small (<6 mm) and intermediate (6-12 mm) nodules. CT guided biopsy of peripheral lesions, either through the chest wall (80%) or by means of a bronchoscope (20%) yields only a 0.001-0.002 cm2 of diagnostic tissue, and as such, cancer, when present, is only successfully identified in 60% of small and intermediate nodules. Although bronchoscopic techniques and technology continue to evolve, biopsy accuracy, specificity, and sensitivity will always be limited when dealing with small and intermediate nodules in the periphery of the lung.

If it is determined that the lesion is cancerous, a second procedure may be performed to remove the lesion and then followed up with chemotherapy and/or radiation. The second procedure most likely involves lung surgery. These procedures are typically done through an incision between the ribs. There are a number of possible procedures depending on the state of the cancer. Video-assisted thoracic surgery is a less invasive procedure for certain types of lung cancer. It is performed through small incisions utilizing an endoscopic approach and is typically utilized for performing wedge resections of smaller lesions close to the surface of a lung. In a wedge resection, a portion of the lobe is removed. In a sleeve resection, a portion of a large airway is removed thereby preserving more lung function.

Nodules deeper than 2-3 cm from the lung surface, once identified as suspicious for cancer, are difficult to localize and excise using laparoscopic or robotic lung sparing technique despite pre-procedure image guided biopsy and localization. Thus, surgeons perform an open thoracotomy or lobectomy to remove lung nodules that are 2-3 cm from the lung surface. A thoracotomy is an open approach surgery in which a portion of a lobe, a full lobe or an entire lung is removed. In a pneumonectomy, an entire lung is removed. This type of surgery is obviously the most aggressive. In a lobectomy, an entire section or lobe of a lung is removed and represents a less aggressive approach than removing the entire lung. All thoracoscopic lung surgeries require trained and experienced thoracic surgeons and the favorability of surgical outcomes track with operative experience.

Any of these types of lung surgery is a major operation with possible complications which depend on the extent of the surgery as well as the patient's overall health. In addition to the reduction in lung function associated with any of these procedures, the recovery may take from weeks to months. With a thoracotomy, spreading of the ribs is required, thereby increasing postoperative pain. Although video-assisted thoracic surgery is less invasive, there can still be a substantial recovery period. In addition, once the surgery is complete, full treatment may require a system chemotherapy and/or radiation treatment.

As set forth above, a fine needle biopsy may not prove to be totally diagnostic. The fine needle biopsy procedure involves guiding a needle in three-dimensional space under two-dimensional imaging. Accordingly, the doctor may miss the lesion, or even if he or she hits the correct target, the section of the lesion that is removed through the needle may not contain the cancerous cells or the cells necessary to assess the aggressiveness of the tumor. A needle biopsy removes enough tissue to create a smear on a slide. The device of the present disclosure is designed to remove the entire lesion, or a substantial portion of it, while minimizing the amount of healthy lung tissue removal. This offers a number of advantages. Firstly, the entire lesion may be examined for a more accurate diagnosis without confounding sampling error, loss of cell packing or gross architecture. Secondly, since the entire lesion is removed, a secondary procedure as described above may not be required. Thirdly, localized chemotherapy and/or energy-based tumor extirpation, such as radiation, may be introduced via the cavity created by the lesion removal.

In at least one embodiment, the disclosure defines a method for removing a tissue lesion including anchoring to the tissue lesion; creating a channel in the tissue leading to the tissue lesion; creating a tissue core including the tissue lesion; ligating the tissue core at a ligation point downstream from the tissue lesion; amputating the tissue core form the tissue between the ligation point and the tissue lesion; and removing the tissue core from the channel.

In keeping with aspects of the disclosure, the sleeve may be inserted in the channel prior to or after removing the tissue core. The sleeve may also be anchored to the tissue. In keeping with another aspect of the disclosure, a localized treatment may be delivered through the sleeve.

In some embodiments, creating a tissue core includes cauterizing and cutting tissue. Ligating tissue may include tissue may include cauterizing tissue at a specific location known as the ligation point. Amputation of the tissue core may be performed with a snare, an energized wire or any other device capable of slicing tissue.

In some embodiments, the tissue core is created by first sealing blood vessels then slicing tissue to form the core.

BRIEF DESCRIPTION OF THE DRAWINGS

The following drawings show generally, by way of example, but not by way of limitation, various examples discussed in the present disclosure. In the drawings.

DETAILED DESCRIPTION

Figure 1:
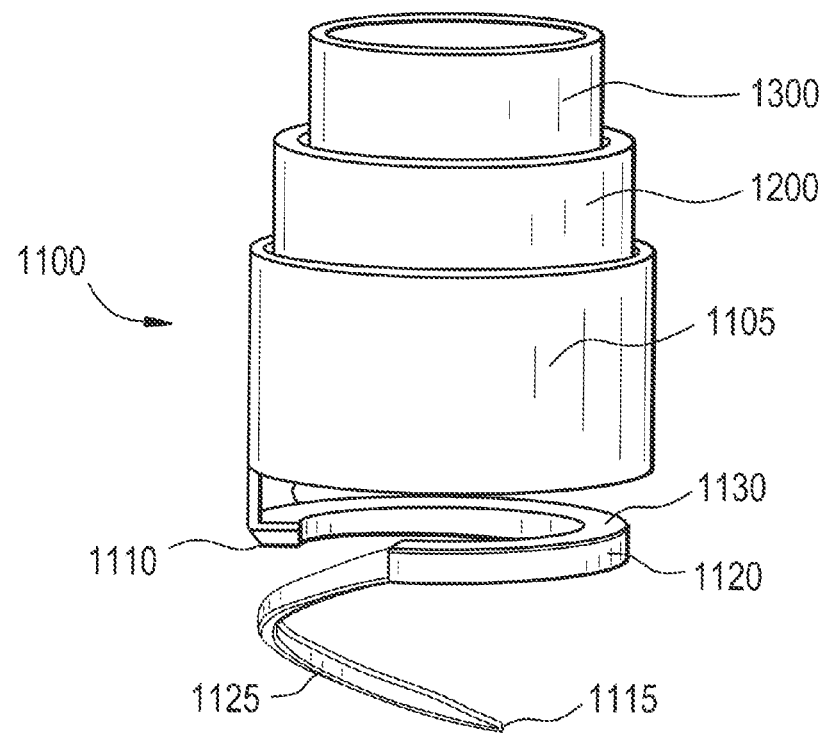
FIG. 1 depicts a tissue resection device in accordance with an embodiment of the present disclosure.

The present disclosure relates to systems and methods for coring tissue. Various tissue and sites may benefit from the disclosed systems and methods.

A core of tissue may have a prescribed (e.g., pre-defined) shape (e.g., columnar) and dimension based on a coring apparatus. Such coring apparatus may be used to core the same or substantially the same shaped tissue core in a repeatable manner. Such coring may be distinguished from other tissue removal, for example using scissors or scalpel, where the cut tissue will not have a pre-defined shape or dimensions.

The present disclosure relates to methods and systems for coring tissue. Methods for coring tissue may comprise disposing a tissue resection device at a target tissue site, causing the tissue resection device to resect a core of tissue from the target tissue site, and removing the core of tissue from the body, wherein the removing the core of tissue from the body creates a core cavity at the target tissue site. The core of tissue comprises at least a portion of a tissue lesion. The resecting the core of tissue from the target tissue site may comprise mechanical transection. The resecting the core of tissue from the target tissue site may comprise the delivery of radiofrequency energy. The resecting the core of tissue from the target tissue site may comprise mechanical compression and the delivery of radiofrequency energy. The resecting the core of tissue from the target tissue site may comprise transection with an energized wire. The resecting the core of tissue from the target tissue site may comprise one of more of mechanical compression, the delivery of radiofrequency energy, the delivery of microwave energy, the delivery of ultrasonic energy, or transection with an energized wire. Other resection devices and procedures may be used. The resection device may be configured for one or more of mechanical compression, the delivery of radiofrequency energy, the delivery of microwave energy, the delivery of ultrasonic energy, or transection with an energized wire.

The present disclosure relates to methods and systems for coring tissue and sealing the core cavity created by removing the tissue core. Such methods may comprise disposing a fill material in the core cavity. Methods may comprise applying pressure to a portion of the core cavity such as to a wall defining the core cavity. Methods may comprise ablating a portion of the core cavity such as a wall defining the core cavity. Methods may comprise causing a cavity closure device, such as suture thread, a stapling device, an ultrasonic tissue sealing device, a bipolar radiofrequency sealing device, or any combination thereof to close the tissue cavity. Methods may comprise disposing a cavity sealing material, such as a tissue graft, a hemostatic patch, a hemostatic agent such as fibrin or thrombin, a biological adhesive material such as Dermabond®, or any combination thereof to close the tissue cavity.

Methods may comprise coring and sealing blood vessel simultaneously as coring procedure is implemented. For example, radiofrequency energy may be provided between the coil and anvil electrodes. As a further example, a coil may be rotated into a target site, an anvil electrode may be cause to close against the coil, a radiofrequency energy may be used to seal areas adjacent the target site, and tissue may be cored using a cutting blade. Such a sequence may be repeated until the cored tissue is within a cutting tube. At this point, ligation (e.g., with another set of electrodes) may be performed to seal any potential blood vessel connecting the cored tissue with surrounding tissue. In an aspect, a mechanical ligation line may be deployed to finish the coring process so that cored tissue can be removed, leaving the cored cavity ready for any subsequent step.

Methods may comprise any combination or permutation of: 1) disposing an anchoring device into a tissue cavity, 2) disposing a tissue access port into the tissue cavity, 3) disposing a tissue sealing device into the tissue cavity (with or without a tissue access port, with or without guidance from an anchoring device), 4) causing the tissue sealing device to seal at least a portion of the tissue cavity, 5) introducing a fill material into the tissue cavity (with or without a fill material delivery device, with or without being preceded by disposing a tissue sealing device into the tissue cavity, with or without removing the tissue sealing device after sealing at least a portion of the tissue cavity, with or without a tissue access port), 6) disposing a cavity sealing material adjacent to the tissue cavity (with or without being preceded by disposing a tissue sealing device into the tissue cavity, with or without removing the tissue sealing device after sealing at least a portion of the tissue cavity, with or without being preceded by introducing a fill material into the tissue cavity), 7) disposing a cavity closure device adjacent to the tissue, and 8) causing a cavity closure device to close the tissue cavity (with or without being preceded by any combination or permutation of the above steps). As described herein, methods may be used to core and/or seal tissue at various target sites. Although a lung is used as an illustrative example, it should not be so limiting, as other target sites may be punctured or actively cored and may benefit from the disclosed sealing methods.

Various methods, devices, and systems may be used to core or remove tissue.

A method for removing a tissue lesion may comprise introducing a tissue resection device to a target tissue site, causing the tissue resection device to resect a core of tissue from the target tissue site, and removing the core of tissue from the body. The core of tissue may comprises at least a portion of a tissue lesion. A method may further comprise creating a core cavity at the target tissue site. A method may further comprise inserting a sleeve into the core cavity. A method may further comprise delivering radiofrequency energy through the core cavity. A method may further comprise delivering chemotherapy through the core cavity. A method may further comprise delivering microwave radiation through the core cavity. A method may further comprise delivering thermal energy through the core cavity. A method may further comprise delivering ultrasonic energy through the core cavity. The tissue resection device may be configured for the delivery of radiofrequency energy. The tissue resection device may be configured for mechanical transection. The tissue resection device may comprise mechanical compression and the delivery of radiofrequency energy. A method may further comprise amputating the core of tissue from the target tissue site. As an example, the means for amputation of the core of tissue may comprise mechanical transection. As a further example, the means for amputation of the core of tissue may comprise the delivery of radiofrequency energy. The means for amputation of the core of tissue may comprise mechanical compression and the delivery of radiofrequency energy. The means for amputation of the core of tissue may comprise transection with an energized wire. Other devices may be used.

A method for removing a core of tissue may comprise introducing a tissue resection device to a target tissue site, causing the tissue resection device to resect a core of tissue from the target tissue site, and removing the core of tissue from the body. A method may further comprise creating a core cavity at the target tissue site. A method may further comprise inserting a sleeve into the core cavity. A method may further comprise delivering radiofrequency energy through the core cavity. A method may further comprise delivering chemotherapy through the core cavity. A method may further comprise delivering microwave radiation through the core cavity. A method may further comprise delivering thermal energy through the core cavity. A method may further comprise delivering ultrasonic energy through the core cavity. The tissue resection device may be configured for the delivery of radiofrequency energy. The tissue resection device may be configured for mechanical transection. The tissue resection device may be configured for mechanical compression and the delivery of radiofrequency energy. A method may further comprise amputating the core of tissue from the target tissue site. The means for amputation of the core of tissue may comprise mechanical transection. The means for amputation of the core of tissue may comprise the delivery of radiofrequency energy. The means for amputation of the core of tissue may comprise mechanical compression and the delivery of radiofrequency energy. The means for amputation of the core of tissue may comprise transection with an energized wire.

A method for removing a core of tissue may comprise introducing a tissue resection device to a target tissue site. The tissue resection device may comprise one or more of: a first clamping element comprising a helical coil and a first electrode, or a second clamping element comprising a second electrode. Where a second clamping element is included, the second clamping element may be positioned to oppose at least a portion of the first clamping element. The method may further comprise causing the tissue resection device to resect a core of tissue from the target tissue site and removing the core of tissue from the body. A method may further comprise creating a core cavity at the target tissue site. A method may further comprise inserting a sleeve into the core cavity. A method may further comprise delivering radiofrequency energy through the core cavity. A method may further comprise delivering chemotherapy through the core cavity. A method may further comprise delivering microwave radiation through the core cavity. A method may further comprise delivering thermal energy through the core cavity. A method may further comprise delivering ultrasonic energy through the core cavity. The tissue resection device may be configured for resecting the core of tissue comprises the delivery of radiofrequency energy. The tissue resection device may be configured for resecting the core of tissue comprises mechanical transection. The tissue resection device may be configured for resecting the core of tissue comprises mechanical compression and the delivery of radiofrequency energy. A method may further comprise amputating the core of tissue from the target tissue site. The means for amputation of the core of tissue may comprise mechanical transection. The means for amputation of the core of tissue may comprise the delivery of radiofrequency energy. The means for amputation of the core of tissue may comprise mechanical compression and the delivery of radiofrequency energy. The means for amputation of the core of tissue may comprise transection with an energized wire.

A method for sealing biological fluid vessels may comprise piercing a target tissue site containing a least a portion of at least one target biological fluid vessel with a helical tissue sealing mechanism, wherein the helical tissue sealing mechanism comprises: a helical piercing element and a clamping element. Wherein the method may comprise causing the helical tissue sealing mechanism to apply mechanical compression to at least one target biological fluid vessel and delivering energy to seal at least one target biological fluid vessel. The helical piercing element may comprise the clamping element. The mechanical compression may be applied between the helical piercing element and the clamping element. A method may further comprise a second clamping element. The mechanical compression may be applied between the first and second clamping elements. The delivered energy may comprise monopolar radiofrequency energy. The delivered energy may comprise bipolar radiofrequency energy. The delivered energy may comprise thermal energy. The delivered energy comprises ultrasonic energy.

A method for sealing biological fluid vessels may comprise piercing a target tissue site with a helical piercing element, adjusting the pitch of the helical piercing element to apply mechanical compression to the target tissue, and delivering energy to seal at least one biological fluid vessel in the target tissue. The helical piercing element may comprise a plurality of tissue sealing electrodes. The delivered energy may comprise monopolar radiofrequency energy. The delivered energy may comprise bipolar radiofrequency energy. The delivered energy may comprise thermal energy. The delivered energy may comprise ultrasonic energy.

A tissue resection apparatus may comprise a first clamping element comprising a helical coil, a second clamping element, the second clamping element being positioned to oppose at least a portion of the first clamping element, a first and second electrode configured for the delivery of radiofrequency energy for sealing tissue, and a cutting element configured for the transection of at least a portion of the sealed tissue. A tissue resection device may further comprise: a first actuator operable to actuate the first or second clamping element to apply mechanical compression to tissue and a second actuator operable to actuate the cutting element to transect tissue. The helical coil may include first and second contiguous coil segments. The first coil segment may comprise a generally planar open ring. The first coil segment may be helical and may have a pitch of zero. The second coil segment may be helical and may have a non-zero pitch. The second coil segment may have a variable pitch. The first coil segment may be helical and may have a first pitch and the second coil segment may be helical and may have a second pitch, and at least one of the first and second pitches may be variable. The first electrode may be comprised by at least a portion of the first clamping element. The second electrode may be comprised by at least a portion of the second clamping element. The helical coil may comprise a blunt tip. The first and second electrodes may comprise surface profiles that are matching or substantially matching. At least a portion of the cutting element may comprise a sharpened edge. The cutting element may comprise at least one electrode configured for the delivery of radiofrequency energy. The cutting element may comprise an ultrasonic blade. The tissue resection device may further comprise a second cutting element configured for the amputation the core of tissue from the target tissue site. At least a portion of the second cutting element may comprise a sharpened edge. The second cutting element may comprise at least one electrode configured for the delivery of radiofrequency energy. The second cutting element may comprise an energized wire. The second cutting element may comprises a suture. The tissue resection device may further comprise an actuator operable to actuate the second cutting element to transect tissue.

A tissue resection apparatus may comprise a first clamping element having a helical coil disposed on a distal end, a second clamping element, the second clamping element being positioned to oppose at least a portion of the first clamping element, a first and second electrode configured for the delivery of radiofrequency energy for sealing tissue, and a cutting element configured for the transection of at least a portion of the sealed tissue. The tissue resection device may further comprise a first actuator operable to actuate the first or second clamping element to apply mechanical compression to tissue and a second actuator operable to actuate the cutting element to transect tissue. The helical coil may comprise first and second contiguous coil segments. The first coil segment comprises a generally planar open ring. The first coil segment may be helical and may have a pitch of zero. The second coil segment may be helical and may have a non-zero pitch. The second coil segment may have a variable pitch. The first coil segment may be helical and may have a first pitch and the second coil segment may be helical and may have a second pitch, and at least one of the first and second pitches may be variable. The first electrode may be comprised by at least a portion of the helical coil. The first electrode may be comprised by at least a portion of the first clamping element. The second electrode may be comprised by at least a portion of the second clamping element. The helical coil may comprise a blunt tip. The first and second electrodes may comprise surface profiles that are matching or substantially matching. At least a portion of the cutting element may comprise a sharpened edge. The cutting element may comprise at least one electrode configured for the delivery of radiofrequency energy. The cutting element may comprise an ultrasonic blade. The tissue resection device may further comprise a second cutting element configured for the amputation the core of tissue from the target tissue site. At least a portion of the second cutting element may comprise a sharpened edge. The second cutting element may comprise at least one electrode configured for the delivery of radiofrequency energy. The second cutting element may comprise an energized wire. The second cutting element may comprise a suture. The tissue resection device may further comprise an actuator operable to actuate the second cutting element to transect tissue.

A tissue resection apparatus may comprise a first clamping element comprising a helical coil and a first electrode, and a second clamping element comprising a second electrode, the second clamping element being positioned to oppose at least a portion of the first clamping element. The first and second clamping elements may be configured for: (a) the delivery of radiofrequency energy for sealing tissue, and (b) the application of mechanical compression for the transection of tissue. The tissue resection device may further comprise a first actuator operable to actuate the first or second clamping element to apply mechanical compression to tissue and a second actuator operable to actuate the cutting element to transect tissue. The helical coil may comprise first and second contiguous coil segments. The first coil segment may comprise a generally planar open ring. The first coil segment may be helical and may have a pitch of zero. The second coil segment may be helical and may have a non-zero pitch. The second coil segment may have a variable pitch. The first coil segment may be helical and may have a first pitch and the second coil segment may be helical and may have a second pitch, and at least one of the first and second pitches may be variable. The first electrode may be comprised by at least a portion of the helical coil. The first electrode may be comprised by at least a portion of the first clamping element. The second electrode may be comprised by at least a portion of the second clamping element. The helical coil may comprise a blunt tip. The first and second electrodes may comprise surface profiles that are matching or substantially matching. At least a portion of the cutting element may comprise a sharpened edge. The cutting element may comprise at least one electrode configured for the delivery of radiofrequency energy. The cutting element may comprise an ultrasonic blade. The tissue resection device may further comprise a second cutting element configured for the amputation the core of tissue from the target tissue site. At least a portion of the second cutting element may comprise a sharpened edge. The second cutting element may comprise at least one electrode configured for the delivery of radiofrequency energy. The second cutting element may comprise an energized wire. The second cutting element may comprise a suture. The tissue resection device may further comprise an actuator operable to actuate the second cutting element to transect tissue.

A surgical instrument system for the resection of tissue may comprise an end effector operable to cut and seal tissue, wherein the end effector and a generator configured to provide power to the end effector having the first and second electrodes for sealing tissue. The end effector may comprise a first clamping element comprising a helical coil, a second clamping element, the second clamping element being positioned to oppose at least a portion of the first clamping element, a first and second electrode configured for the delivery of radiofrequency energy for sealing tissue, and a cutting element configured for the transection of at least a portion of the sealed tissue. The surgical instrument system may further comprise a controller in communication with the generator, wherein the controller is configured to control the generator to provide radiofrequency energy sufficient to seal tissue to the first and second electrodes of the end effector, based on at least one sensed operating condition of the end effector. The controller may be configured to sense the presence of tissue at the end effector. The controller may be configured to sense the presence of tissue at the end effector based on a measured impedance level associated with the first and second electrodes. The controller may be configured to sense an amount of force applied to at least one of the first or second clamping elements to detect the presence of tissue at the end effector. The controller may be configured to sense the position of the cutting element relative to at least one of the first or second clamping elements. The controller may be configured to control the generator to provide radiofrequency energy at the end effector when the second actuator is actuated and no tissue is sensed at the end effector. The controller may be configured to control the generator to provide a continuous amount of radiofrequency energy. The controller may be configured to control the generator to automatically provide an increase or decrease in the amount of radiofrequency energy. The system may further comprise: a first actuator operable to actuate the first or second clamping element to apply mechanical compression to tissue; and; a second actuator operable to actuate the cutting element to transect tissue. The helical coil may comprise first and second contiguous coil segments, the first coil segment including the first electrode. The first coil segment may comprise a generally planar open ring. The first coil segment may be helical and may have a pitch of zero. The second coil segment may be helical and may have a non-zero pitch. The second coil segment may have a variable pitch. The first coil segment may be helical and may have a first pitch and the second coil segment may be helical and may have a second pitch, and at least one of the first and second pitches may be variable. The first electrode may be comprised by at least a portion of the helical coil. The first electrode may be comprised by at least a portion of the first clamping element. The second electrode may be comprised by at least a portion of the second clamping element. The helical coil may comprise a blunt tip. The first and second electrodes may comprise surface profiles that are matching or substantially matching. At least a portion of the cutting element may comprise a sharpened edge. The cutting element may comprise at least one electrode configured for the delivery of radiofrequency energy. The cutting element may comprise an ultrasonic blade. The tissue resection device may further comprise a second cutting element configured for the amputation the core of tissue from the target tissue site. At least a portion of the second cutting element may comprise a sharpened edge. The second cutting element may comprise at least one electrode configured for the delivery of radiofrequency energy. The second cutting element may comprise an energized wire. The second cutting element may comprise a suture. The tissue resection device may further comprise an actuator operable to actuate the second cutting element to transect tissue.

A tissue resection apparatus may comprise a first clamping element comprising a helical coil, a second clamping element, the second clamping element being positioned to oppose at least a portion of the first clamping element, a first and second electrode configured for the delivery of radiofrequency energy for sealing tissue, a first cutting element configured for the transection of at least a portion of the sealed tissue, a first and second ligating element, and a second cutting element positioned between said first and second ligating elements. The tissue resection device may further comprise a first actuator operable to actuate the first or second clamping element to apply mechanical compression to tissue, and a second actuator operable to actuate the cutting element to transect tissue. The helical coil may comprise first and second contiguous coil segments. The first coil segment may comprise a generally planar open ring. The first coil segment may be helical and may have a pitch of zero. The second coil segment may be helical and may have a non-zero pitch. The second coil segment may have a variable pitch. The first coil segment may be helical and may have a first pitch and the second coil segment may be helical and may have a second pitch, and at least one of the first and second pitches may be variable. The first electrode may be comprised by at least a portion of the helical coil. The first electrode may be comprised by at least a portion of the first clamping element. The second electrode may be comprised by at least a portion of the second clamping element. The helical coil may comprise a blunt tip. The first and second electrodes may comprise surface profiles that are matching or substantially matching. At least a portion of the cutting element may comprise a sharpened edge. The cutting element may comprise at least one electrode configured for the delivery of radiofrequency energy. The cutting element may comprise an ultrasonic blade. The tissue resection device may further comprise a second cutting element configured for the amputation the core of tissue from the target tissue site. At least a portion of the second cutting element may comprise a sharpened edge. The second cutting element may comprise at least one electrode configured for the delivery of radiofrequency energy. The second cutting element may comprise an energized wire. The second cutting element may comprise a suture. The tissue resection device may further comprise an actuator operable to actuate the second cutting element to transect tissue.

A tissue sealing mechanism may comprise a helical coil with a generally obround cross section and a tapered point disposed at a distal end, a first and second helical tissue sealing surface, wherein the first and second helical tissue sealing surfaces are provided by the parallel planar surfaces of the helical coil, a first electrode disposed on the first helical tissue sealing surface, and a second electrode disposed on the second helical tissue sealing surface, wherein the first and second electrodes are configured to apply bipolar radiofrequency energy for sealing tissue. The helical coil may comprise first and second contiguous coil segments. The helical coil may comprise a blunt tip. The first and second electrodes may have surface profiles that are substantially matching. The first and second helical tissue sealing surfaces may further comprise a plurality of electrodes configured for the delivery of bipolar radiofrequency energy.

FIGS. 1-7 show examples devices that may be used to effect a coring process, as described herein. For example, a resection device of the present disclosure may comprise an energy-based arrangement capable of penetrating tissue towards a target lesion. In one embodiment depicted in FIG. 1, tissue resection device 1100 includes an outer tube 1105 is provided having a distal edge profile and having an inner diameter IDouter. A coil 1110 is attached to the outer tube 1105 where the coil turns are spaced from and opposed to a distal end of the outer tube 1105. The coil 1110 preferably has a slightly blunted tip 1115 to minimize the possibility that it will penetrate through a blood vessel while being sufficiently sharp to penetrate tissue such as pleura and parenchyma. In some embodiments, the coil 1110 may take the form of a helix having a constant or variable pitch. The coil 1110 may also have a variable cross-sectional geometry. An electrode 1130 is disposed on a surface or embedded within the coil 1110.

In some embodiments, as illustrated in FIG. 1, the coil 1110 may include a plurality of contiguous coil segments, e.g., coil segments 1120 and 1125. Coil segment 1120 comprises a helical member having a pitch of zero, e.g., a generally planar open ring structure, having an inner diameter IDcoil and an outer diameter ODcoil. Coil segment 1125 comprises a helical structure of constant or variable pitch and constant or variable cross-sectional geometry. In this embodiment, the electrode 1130 may be disposed on a surface of or embedded in coil segment 1120.

Figure 2:
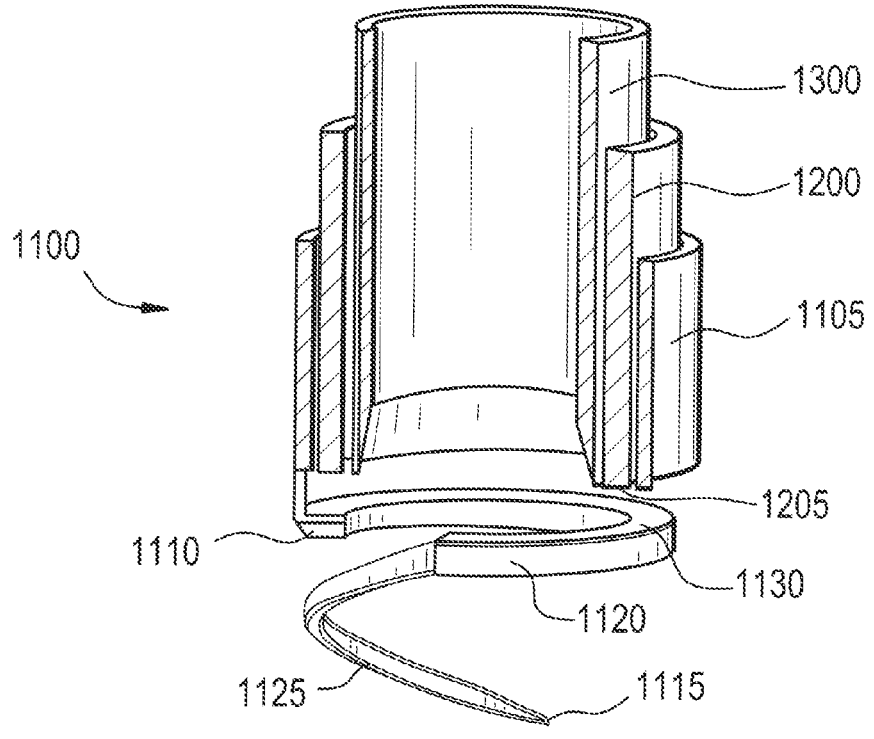
FIG. 2 illustrates a sectional view of the tissue resection device of FIG. 1.

A central tube 1200 is provided having a distal end with an edge profile comprising one or more surface segments and having an outer diameter ODcentral and an inner diameter IDcentral. As illustrated in FIG. 2, an electrode 1205 is disposed on or embedded within at least one of the surface segments. The central tube 1200 is slidably disposed within the outer tube 1105 and positioned such that electrode 1205 opposes and overlaps at least a portion of electrode 1130. The space between electrode 1205 and electrode 1130 is referred to as the tissue clamping zone. In keeping with an aspect of the present disclosure, ODcentral>IDcoil and ODcoil>IDcentral. In some embodiments, ODcentral is about equal to ODcoil. Accordingly, the central tube 1200 may be advanced through the tissue clamping zone towards the coil 1110 such that electrode 1205 abuts electrode 1130.

A cutting tube 1300 is slidably disposed within central tube 1200. The distal end of the cutting tube 1300 is provided with a knife edge to facilitate tissue cutting.

To enable tissue resection, the resection device 1100 may be inserted into tissue and the outer tube 1105 may be advanced a predetermined distance towards a target. Coil segment 1125 allows the device to penetrate the tissue in a manner similar to a cork screw. As coil segment 1125 penetrates tissue, any vessel in its path is either moved planar to the coil segment 1120 or pushed away from the coil 1100 for subsequent turns. The coil tip 1115 is made blunt enough to minimize chances that it will penetrate through a blood vessel while still sharp enough to penetrate certain tissue such as the lung pleura and parenchyma. The central tube 1200 may then be advanced a predetermined distance towards the target. Any vessels that are disposed in the tissue clamping zone will be clamped between electrode 1130 and electrode 1205. The vessels can then be sealed by the application of bipolar energy to electrode 1130 and electrode 1205. Once blood vessels are sealed, the cutting tube 1300 is advanced to core the tissue to the depth that the outer tube 1105 has reached. The sealing and cutting process can be repeated to create a core of desired size.

Figure 3:
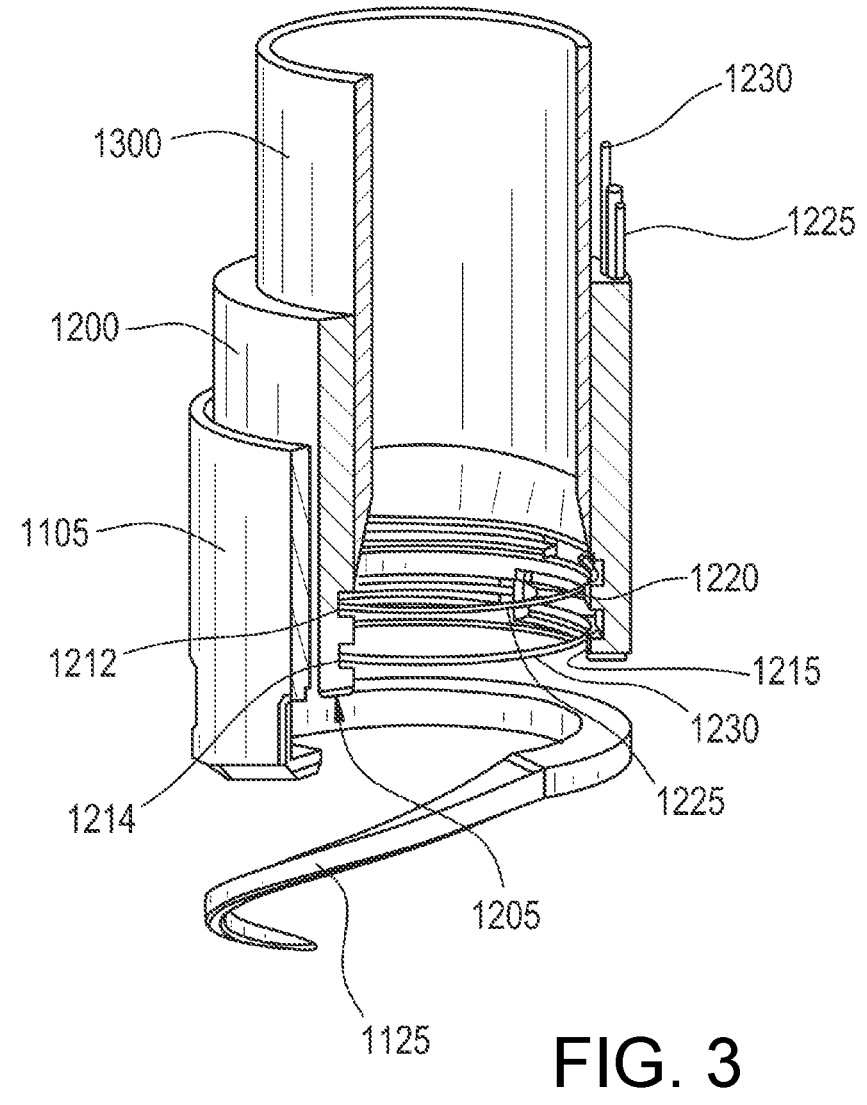
FIG. 3 shows a sectional view of a tissue resection device in accordance with an embodiment of the present disclosure.
Figure 4:
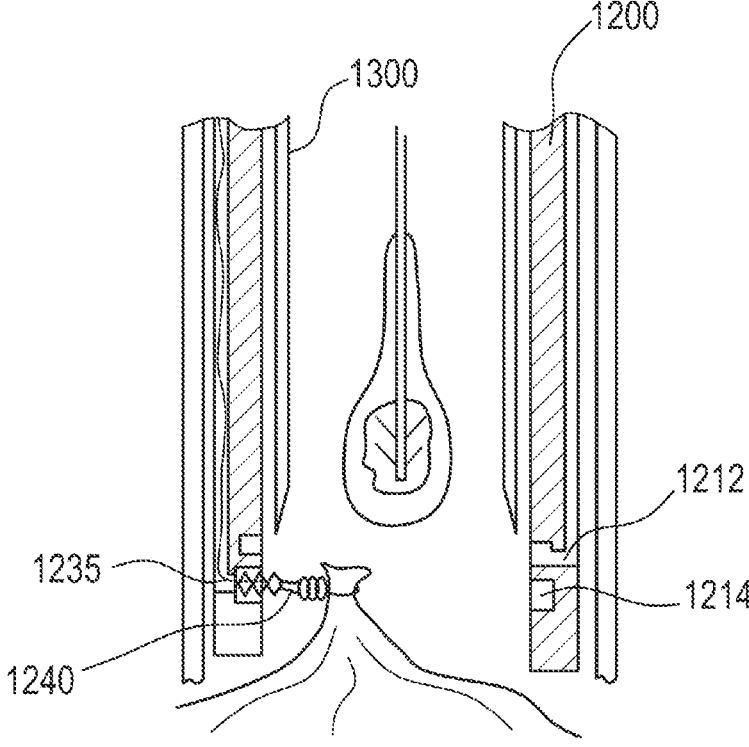
FIG. 4 depicts a sectional view of a tissue resection device in accordance with an embodiment of the present disclosure.

In keeping with an aspect of the present disclosure, the resection device 1100 may be further configured to dissect a target lesion and seal tissue proximate the dissection point. To facilitate dissection and sealing, as illustrated in FIG. 3, the central tube 1200 is provided with a ligation snare 1230, first and second ligation electrodes 1215 and 1220, and an amputation snare 1225. As used herein, the word "snare" refers to a flexible line, e.g., a string or a wire. The inner wall surface of the central tube 1200 includes upper and lower circumferential grooved pathways 1212 and 1214 disposed proximate the distal end. The first and second ligation electrodes 1215 and 1220 are disposed on the inner wall of the central tube 1200 such that lower circumferential groove 1214 is between them. Upper grooved pathway 1212 is disposed axially above the ligation electrodes 1215 and 1220.

The ligation snare 1230 is disposed in lower circumferential groove 1214 and extends through the central tube 1200 and axially along the outer wall surface to a snare activation mechanism (not shown). Amputation snare 1225 is disposed in upper circumferential groove 1212 and extends through the central tube 1200 and axially along the outer wall surface to a snare activation mechanism (not shown). The outer surface of the central tube 1200 may be provided with a plurality of axially extending grooved pathways which receive the amputation snare 1225, the ligation snare 1230 and are in communication with upper and lower circumferential grooved pathways 1212 and 1214. In addition, electrode leads for the ligation electrodes 1215 and 1220 may extend to an energy source via the axially extending grooved pathways.

In operation, the resection device 1100 of this embodiment can detach and seal the tissue core. The cutting tube 1300 may be retracted to expose the ligation snare 1230 which is preferably made of flexible line, e.g., suture. The ligation snare 1230 may be engaged to snag tissue and pull tissue against the inner wall surface between first and second ligation electrodes 1215 and 1220. Bipolar energy is then applied to first and second electrodes 1215 and 1220 to seal, i.e., cauterize, the tissue. Once sealed, the cutting tube 1300 may be further retracted to expose the amputation snare 1225 which may then be activated to sever the tissue core upstream from the point where the tissue was sealed (ligation point). In some embodiments, the amputation snare 1225 has a smaller diameter than that of the ligation snare 1230. The smaller diameter facilitates tissue slicing. Accordingly, the resection device 1100 according to this embodiment both creates a tissue core and disengages the core from surrounding tissue.

In an alternative embodiment, the resection device 1100 of the present disclosure is provided with a single snare disposed between the ligation electrodes which both ligates and cuts tissue. In this embodiment, the single snare first pulls tissue against the inner wall surface of the central tube 1200 between the ligation electrodes 1215 and 1220. Bipolar energy is then applied to the first and second electrodes 1215 and 1220 to seal, i.e., cauterize, the tissue. Once sealed, the snare is further pulled to sever the tissue core.

In yet another embodiment, cutting and sealing may be performed without employing electrodes. In this embodiment, the ligation snare 1230 includes a set of knots 1235 and 1240 which tighten under load, shown, for example, in FIG. 4. Ligation is performed by retracting the cutting tube 1300 to expose the ligation snare 1230 and activating the ligation snare 1230 which lassos tissue as the ligation knot tightens. Once the tissue is lassoed, the cutting tube 1300 may be further retracted to expose amputation snare 1225 which may then be activated to sever the tissue core upstream from the point where the point where the tissue was lassoed.

The present disclosure also contemplates a method and system for using the resection device to remove tissue lesions, for example, lung lesions. The method generally comprises anchoring the lesion targeted for removal, creating a channel in the tissue leading to the target lesion, creating a tissue core which includes the anchored lesion, ligating the tissue core and sealing the surrounding tissue, and removing the tissue core including the target lesion from the channel.

Anchoring may be performed by any suitable structure for securing the device to the lung. Once the lesion is anchored, a channel may be created to facilitate insertion of the resection device 1100. The channel may be created by making an incision in the lung area and inserting a tissue dilator and port into the incision. A tissue core which includes the anchored lesion may be created. In keeping with the present disclosure, the resection device 1100 may be used to create the tissue core, to ligate the tissue core and to seal the tissue core and sever it from the surrounding tissue as described hereinabove. The tissue core may then be removed from the channel. As an example, a cavity port may be inserted in the channel to facilitate subsequent treatment of the target lesion site through chemotherapy and/or energy-based tumor extirpation such as radiation. As a further example, a cavity port may be disposed on the perimeter of the tissue resection apparatus. When the apparatus is removed from the tissue site, the cavity port may remain in place or may be removed.

Figure 5:
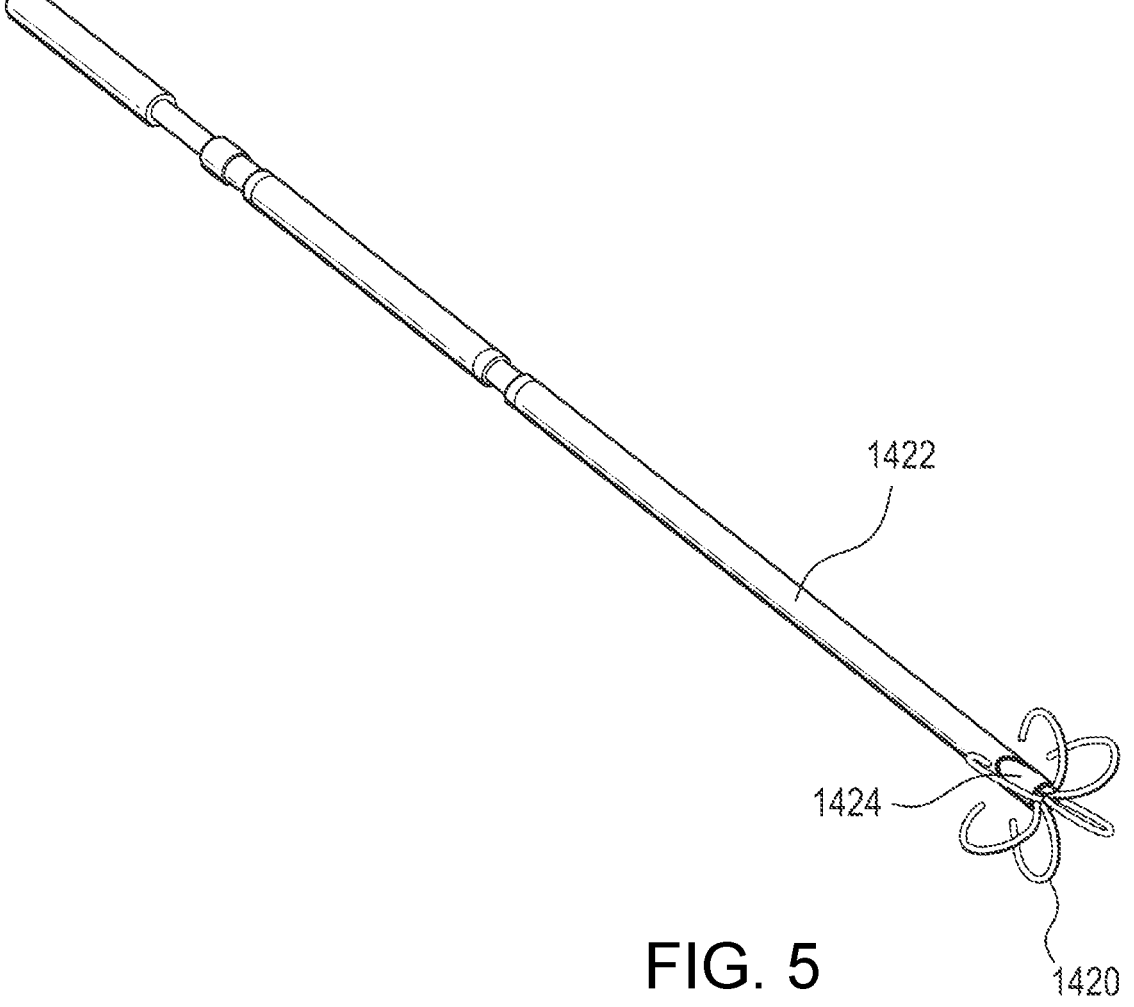
FIG. 5 illustrates an exemplary anchor that may be employed in a lesion removal method in accordance with an embodiment of the present disclosure.

The anchor depicted in FIG. 5 is suitable for use in performing the method for removing tissue lesions described herein. The anchor comprises an outer tube 1422 having a sufficiently sharp edge to pierce the chest cavity tissue and lung without causing excess damage and an inner tube 1424 disposed within the outer tube 1422. One or more tines or fingers 1426 formed from shape memory material, e.g., Nitinol, preformed are attached to the end of the inner tube 1424. The outer tube 1422 is retractably disposed over the inner tube 1424 such that when the outer tube 1422 is retracted, the tines 1426 assume their preform shape as shown. In keeping with the present disclosure, the outer tube 1422 is retracted after it has pierced the lung lesion thereby causing the tines 1426 to engage the lung lesion. Other suitable anchors may include coils and suction-based structures.

Figure 6:
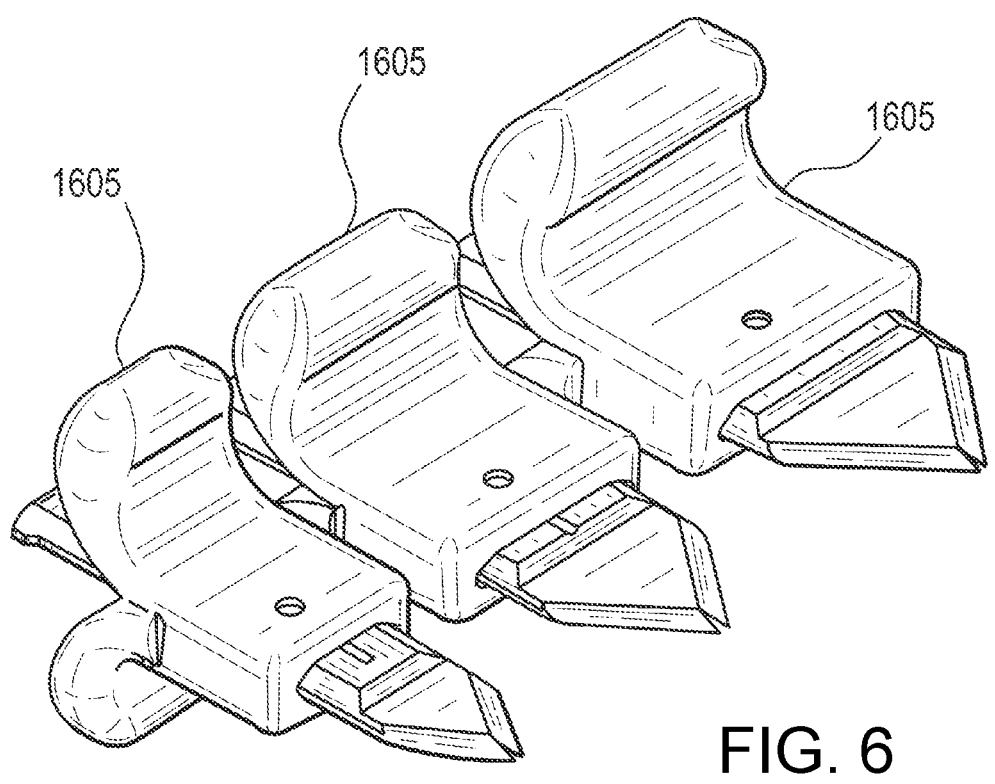
FIG. 6 shows a series of incision blades for use in a lesion removal method in accordance with an embodiment of the present disclosure.

The incision blades depicted in FIG. 6 are suitable for use in performing the method for removing tissue lesions described herein. Once the anchor 1400 is set, it is preferable to create a small cut or incision to facilitate insertion of chest wall tissue dilator. Incision blades 1605 are used to make a wider cut. The incision blades 1605 may be successive and may include a central aperture which allows them to be coaxially advanced along the anchor needle 1405 to create a wider cut in the chest wall, with each successive blade being larger than the previous blade, thereby increasing the width of the incision.

Figure 7:
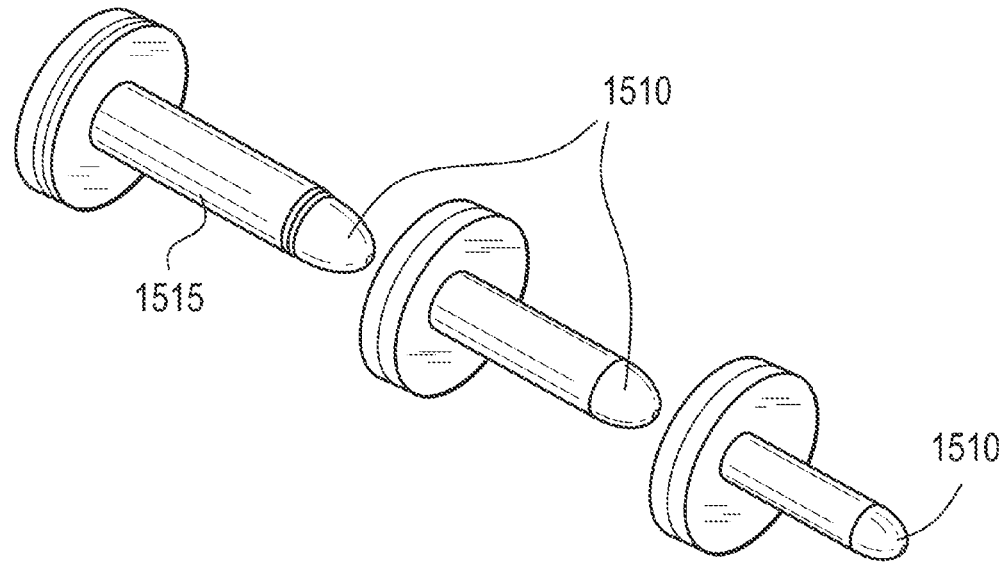
FIG. 7 displays tissue dilators suitable for use in a lesion removal method in accordance with an embodiment of the present disclosure.

The tissue dilator depicted in FIG. 7 is suitable for use in performing the method for removing tissue lesions described herein. The tissue dilator may comprise any suitable device for creating a channel in organic tissue. In one exemplary embodiment, the tissue dilator assembly includes a single cylindrical rod with a rounded end 1510 or a cylindrical rod with rounded end and a rigid sleeve arrangement 1515. Successive tissue dilators are coaxially advanced along the anchor needle to create tissue tract or channel in the chest wall, with each successive dilator being larger than the previous dilator, thereby increasing the diameter of the channel. Once the final dilator with rigid sleeve is deployed, the inner rod 1505 is removed while leaving the rigid sleeve in the intercostal space between ribs to create direct passage to the lung pleura.

Any tissue resection device capable of penetrating lung tissue and creating a tissue core including a target lesion is suitable for use in performing the method for removing tissue lesions described herein. The tissue resection device 1100 described herein is preferred.

Once the tissue resection device 1100 is removed, a small channel in the lung exists where the target lesion was removed. This channel may be utilized to introduce an energy-based ablation device and/or localized chemotherapy depending on the results of the tissue diagnosis. Accordingly, the method and system of the present disclosure may not only be utilized to ensure an effective biopsy is performed but also complete removal of the lesion with minimal healthy lung tissue removal.

Figure 8:
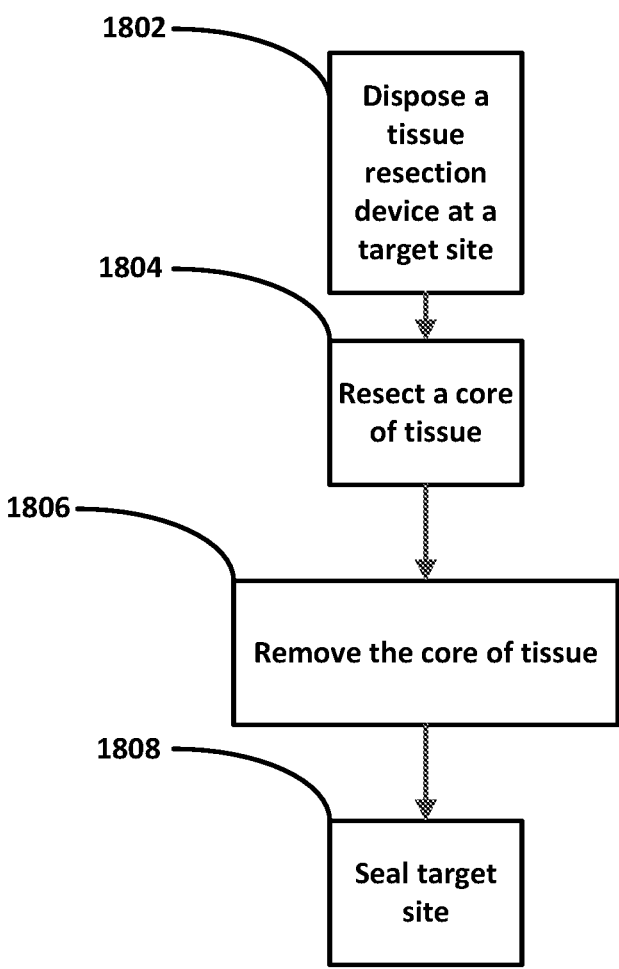
FIG. 8 shows a flow diagram of an example method for coring and for sealing tissue.

FIG. 8 shows a flow diagram of an example method. Tissue at a target site may be cored such that a tissue core is removed from the target site thereby creating a core cavity at the target site. Coring tissue at a target site may comprise transecting and sealing tissue. Coring tissue at a target site may comprise disposing a tissue coring apparatus adjacent to a target tissue site. The tissue coring apparatus may comprise a first clamping element comprising a helical coil, a second clamping element, the second clamping element being positioned to oppose at least a portion of the first clamping element, a first and second electrode configured for the delivery of radiofrequency energy for sealing tissue, and/or a cutting element configured for the transection of at least a portion of the sealed tissue. Other apparatus may be used.

At 1802, a tissue resection device may be disposed at a target tissue site. The target tissue site may comprise a tissue lesion. Various tissues may be comprised as the target site. The tissue resection device may comprise one or more of the devices or components described herein.

At 1804, a core of tissue may be resected. A core of tissue may have a prescribed (e.g., pre-defined) shape (e.g., columnar) and dimension based on a coring apparatus. Such coring apparatus may be used to core the same or substantially the same shaped tissue core in a repeatable manner. Such coring may be distinguished from other tissue removal, for example using scissors or scalpel, where the cut tissue will not have a pre-defined shape or dimensions. As an example, the tissue resection device may be caused to resect a core of tissue from the target tissue site.

At 1806, the tissue resection device may be removed from that body or create a core cavity at the target tissue site. Since a core of tissue was removed, biological fluid may flow toward or into the core cavity.

At 1808, at least a portion of the core cavity may be sealed. Such sealing may comprise sealing biological fluid vessels. The sealing biological fluid vessels may minimize flow of biological fluids into the cavity core.

The present disclosure comprises at least the following aspects:

Aspect 1. A tissue resection device configured for coring tissue, the device comprising: a first clamping element comprising a helical coil; a second clamping element, the second clamping element being positioned to oppose at least a portion of the first clamping element; a first electrode and a second electrode configured for the delivery of radiofrequency energy to an area adjacent one or more of the first clamping element and the second clamping element to seal tissue; and a cutting element configured for the transection of at least a portion of the sealed tissue.

Aspect 2. A method of using the tissue resection device of aspect 1, the method comprising: rotating the helical coil into a target tissue site; causing the first clamping element and the second clamping element to clamp against each other; causing radiofrequency energy to energize one or more of the first electrode and the second electrode; and causing the cutting element to core at least a portion of the target tissue site.

Aspect 3. The tissue resection device of aspect 1, further comprising: a first actuator operable to actuate the first or second clamping element to apply mechanical compression to tissue; and a second actuator operable to actuate the cutting element to transect tissue.

Aspect 4. The tissue resection device of aspect 1, wherein the helical coil comprises first and second contiguous coil segments Aspect 5. The tissue resection device of aspect 4, wherein the first coil segment comprises a generally planar open ring.

Aspect 6. The tissue resection device of aspect 5, wherein the first coil segment is helical and has a pitch of zero.

Aspect 7. The tissue resection device of aspect 4, wherein the second coil segment is helical and has a non-zero pitch.

Aspect 8. The tissue resection device of aspect 7, wherein the second coil segment has a variable pitch.

Aspect 9. The tissue resection device of aspect 4, wherein the first coil segment is helical and has a first pitch and the second coil segment is helical and has a second pitch, and at least one of the first and second pitches is variable.

Aspect 10. The tissue resection device of aspect 1, wherein the first electrode is provided by at least a portion of the first clamping element.

Aspect 11. The tissue resection device of aspect 1, wherein the second electrode is provided by at least a portion of the second clamping element.

Aspect 12. The tissue resection device of aspect 1, wherein the helical coil includes a blunt tip.

Aspect 13. The tissue resection device of aspect 1, wherein the first and second electrodes have surface profiles that are substantially matching.

Aspect 14. The tissue resection device of aspect 1, wherein at least a portion of the cutting element comprises a sharpened edge.

Aspect 15. The tissue resection device of aspect 1, wherein the cutting element comprises at least one electrode configured for the delivery of radiofrequency energy.

Aspect 16. The tissue resection device of aspect 1, wherein the cutting element comprises an ultrasonic blade.

Aspect 17. The tissue resection device of aspect 1, further comprising a second cutting element configured for the amputation the core of tissue from the target tissue site.

Aspect 18. The tissue resection device of aspect 17, wherein at least a portion of the second cutting element comprises a sharpened edge.

Aspect 19. The tissue resection device of aspect 17, wherein the second cutting element comprises at least one electrode configured for the delivery of radiofrequency energy.

Aspect 20. The tissue resection device of aspect 17, wherein the second cutting element comprises an energized wire.

Aspect 21. The tissue resection device of aspect 17, wherein the second cutting element comprises a suture.

Aspect 22. The tissue resection device of aspect 17, further comprising an actuator operable to actuate the second cutting element to transect tissue.

Aspect 23. A method for coring tissue, the method comprising: disposing a tissue resection device at a target tissue site; causing the tissue resection device to resect a core of tissue from the target tissue site; and removing the core of tissue from the body, wherein the removing the core of tissue from the body creates a core cavity at the target tissue site.

Aspect 24. The method of aspect 23, wherein the core of tissue comprises at least a portion of a tissue lesion.

Aspect 25. The method of aspect 23, further comprising disposing a sleeve to provide access to the target tissue site.

Aspect 26. The method of aspect 25, wherein the disposing the sleeve is implemented prior to the removing the core of tissue from the body.

Aspect 27. The method of aspect 25, wherein the disposing the sleeve is implemented after the removing the core of tissue from the body.

Aspect 28. The method of aspect 25, wherein the sleeve comprises a deployable trocar.

Aspect 29. The method of aspect 25, wherein the sleeve comprises electrodes that are configured to seal or ablate adjacent the target tissue site.

Aspect 30. The method of aspect 25, wherein the sleeve comprises radio frequency electrodes that are configured to seal or ablate adjacent the target tissue site using radiofrequency energy.

Aspect 31. The method of aspect 23, further comprising delivering radiofrequency energy to at least a portion of a wall defining the core cavity.

Aspect 32. The method of aspect 23, further comprising delivering chemotherapy to at least a portion of a wall defining the core cavity.

Aspect 33. The method of aspect 23, further comprising delivering microwave energy to at least a portion of a wall defining the core cavity.

Aspect 34. The method of aspect 23, further comprising delivering thermal energy to at least a portion of a wall defining the core cavity.

Aspect 35. The method of aspect 23, further comprising delivering ultrasonic energy to at least a portion of a wall defining the core cavity.

Aspect 36. The method of aspect 23, wherein the tissue resection device is configured for the delivery of radiofrequency energy.

Aspect 37. The method of aspect 23, wherein the tissue resection device is configured for mechanical transection.

Aspect 38. The method of aspect 23, wherein the tissue resection device is configured for mechanical compression and the delivery of radiofrequency energy.

Aspect 39. The method of aspect 23, wherein the resecting the core of tissue from the target tissue site comprises mechanical transection.

Aspect 40. The method of aspect 23, wherein the resecting the core of tissue from the target tissue site comprises the delivery of radiofrequency energy.

Aspect 41. The method of aspect 23, wherein the resecting the core of tissue from the target tissue site comprises mechanical compression and the delivery of radiofrequency energy.

Aspect 42. The method of aspect 23, wherein the resecting the core of tissue from the target tissue site comprises mechanical compression, the delivery of radiofrequency energy, and mechanical transection.

Aspect 43. The method of aspect 23, wherein the resecting the core of tissue from the target tissue site comprises transection with an energized wire.

Aspect 44. The method of aspect 23, further comprising sealing biological fluid vessels.

Aspect 45. The method of aspect 44, wherein the sealing biological fluid vessels minimizes flow of biological fluids into the cavity core.

Aspect 46. The method of aspect 44, wherein the sealing is effected using at least mechanical compression.

Aspect 47. The method of aspect 44, wherein the sealing is effected using at least radiofrequency energy.

Aspect 48. The method of aspect 44, wherein the sealing is effected using at least microwave energy.

Aspect 49. The method of aspect 44, wherein the sealing is effected using at least ultrasonic energy.

Aspect 50. A method for coring tissue, the method comprising: disposing a tissue resection device at a target tissue site, wherein the tissue resection device comprises: a first clamping element comprising a helical coil and a first electrode, and a second clamping element comprising a second electrode, the second clamping element being positioned to oppose at least a portion of the first clamping element; causing the tissue resection device to resect a core of tissue from the target tissue site; and removing the core of tissue from the body, wherein the removing the core of tissue from the body creates a core cavity at the target tissue site.

Aspect 51. The method of aspect 50, wherein the core of tissue comprises at least a portion of a tissue lesion.

Aspect 52. The method of aspect 50, further comprising inserting a sleeve into the core cavity to support a wall of the core cavity.

Aspect 53. The method of aspect 50, further comprising delivering radiofrequency energy to at least a portion of a wall defining the core cavity.

Aspect 54. The method of aspect 50, further comprising delivering chemotherapy to at least a portion of a wall defining the core cavity.

Aspect 55. The method of aspect 50, further comprising delivering microwave energy to at least a portion of a wall defining the core cavity.

Aspect 56. The method of aspect 50, further comprising delivering thermal energy to at least a portion of a wall defining the core cavity.

Aspect 57. The method of aspect 50, further comprising delivering ultrasonic energy to at least a portion of a wall defining the core cavity.

Aspect 58. The method of aspect 50, wherein the tissue resection device is configured for the delivery of radiofrequency energy.

Aspect 59. The method of aspect 50, wherein the tissue resection device is configured for mechanical transection.

Aspect 60. The method of aspect 50, wherein the tissue resection device is configured for mechanical compression and the delivery of radiofrequency energy.

Aspect 61. The method of aspect 50, wherein the resecting the core of tissue from the target tissue site comprises mechanical transection.

Aspect 62. The method of aspect 50, wherein the resecting the core of tissue from the target tissue site comprises the delivery of radiofrequency energy.

Aspect 63. The method of aspect 50, wherein the resecting the core of tissue from the target tissue site comprises mechanical compression and the delivery of radiofrequency energy.

Aspect 64. The method of aspect 50, wherein the resecting the core of tissue from the target tissue site comprises mechanical compression, the delivery of radiofrequency energy, and mechanical transection.

Aspect 65. The method of aspect 50, wherein the resecting the core of tissue from the target tissue site comprises transection with an energized wire.

Aspect 66. The method of aspect 50, further comprising sealing biological fluid vessels.

Aspect 67. The method of aspect 66, wherein the sealing biological fluid vessels minimizes flow of biological fluids into the cavity core.

Aspect 68. The method of aspect 66, wherein the sealing is effected using at least mechanical compression.

Aspect 69. The method of aspect 66, wherein the sealing is effected using at least radiofrequency energy.

Aspect 70. The method of aspect 66, wherein the sealing is effected using at least microwave energy.

Aspect 71. The method of aspect 66, wherein the sealing is effected using at least ultrasonic energy.

Aspect 72. A method for sealing biological fluid vessels, the method comprising: piercing a target tissue site with a helical tissue sealing mechanism, wherein the helical tissue sealing mechanism comprises: a helical piercing element; and at least one clamping element; applying mechanical compression to at least a portion of at least one target biological fluid vessel within the target tissue site; and causing the helical tissue sealing mechanism to seal at least one target biological fluid vessel.

Aspect 73. The method of aspect 72, wherein the helical piercing element comprises at least one clamping element.

Aspect 74. The method of aspect 72, wherein the applying mechanical compression is effected by adjusting the relative positions of the helical piercing element and the clamping element.

Aspect 75. The method of aspect 72, further comprising a second clamping element.

Aspect 76. The method of aspect 75, wherein the applying mechanical compression is effected by adjusting the relative positions of the first and second clamping elements.

Aspect 77. The method of aspect 72, wherein the sealing of at least one target biological fluid vessel minimizes flow of biological fluids through at least one target biological fluid vessel.

Aspect 78. The method of aspect 72, wherein the sealing is effected using at least mechanical compression.

Aspect 79. The method of aspect 72, wherein the sealing is effected using at least radiofrequency energy.

Aspect 80. The method of aspect 72, wherein the sealing is effected using at least microwave energy.

Aspect 81. The method of aspect 72, wherein the sealing is effected using at least ultrasonic energy.

Aspect 82. A tissue resection device configured for coring tissue, the device comprising: a first clamping element having a helical coil disposed on a distal end; a second clamping element, the second clamping element being positioned to oppose at least a portion of the first clamping element; a first and second electrode configured for the delivery of radiofrequency energy, for example, for sealing tissue; and a cutting element configured for the transection of at least a portion of tissue at a target site, such as the sealed tissue.

Aspect 83. The tissue resection device of aspect 82, further comprising: a first actuator operable to actuate the first or second clamping element to apply mechanical compression to tissue; and a second actuator operable to actuate the cutting element to transect tissue.

Aspect 84. The tissue resection device of aspect 82, wherein the helical coil includes first and second contiguous coil segments.

Aspect 85. The tissue resection device of aspect 84, wherein the first coil segment comprises a generally planar open ring.

Aspect 86. The tissue resection device of aspect 85, wherein the first coil segment is helical and has a pitch of zero.

Aspect 87. The tissue resection device of aspect 84, wherein the second coil segment is helical and has a non-zero pitch.

Aspect 88. The tissue resection device of aspect 87, wherein the second coil segment has a variable pitch.

Aspect 89. The tissue resection device of aspect 84, wherein the first coil segment is helical and has a first pitch and the second coil segment is helical and has a second pitch, and at least one of the first and second pitches is variable.

Aspect 90. The tissue resection device of aspect 82, wherein the first electrode is provided by at least a portion of the helical coil.

Aspect 91. The tissue resection device of aspect 82, wherein the first electrode is provided by at least a portion of the first clamping element.

Aspect 92. The tissue resection device of aspect 82, wherein the second electrode is provided by at least a portion of the second clamping element.

Aspect 93. The tissue resection device of aspect 82, wherein the helical coil includes a blunt tip.

Aspect 94. The tissue resection device of aspect 82, wherein the first and second electrodes have surface profiles that are substantially matching.

Aspect 95. The tissue resection device of aspect 82, wherein at least a portion of the cutting element comprises a sharpened edge.

Aspect 96. The tissue resection device of aspect 82, wherein the cutting element comprises at least one electrode configured for the delivery of radiofrequency energy.

Aspect 97. The tissue resection device of aspect 82, wherein the cutting element comprises an ultrasonic blade.

Aspect 98. The tissue resection device of aspect 82, further comprising a second cutting element configured for the amputation the core of tissue from the target tissue site.

Aspect 99. The tissue resection device of aspect 98, wherein at least a portion of the second cutting element comprises a sharpened edge.

Aspect 100. The tissue resection device of aspect 98, wherein the second cutting element comprises at least one electrode configured for the delivery of radiofrequency energy.

Aspect 101. The tissue resection device of aspect 98, wherein the second cutting element comprises an energized wire.

Aspect 102. The tissue resection device of aspect 98, wherein the second cutting element comprises a suture.

Aspect 103. The tissue resection device of aspect 98, further comprising an actuator operable to actuate the second cutting element to transect tissue.

Aspect 104. The tissue resection device of aspect 82, further comprising: a first and second ligating element; and a second cutting element positioned between said first and second ligating elements.

Aspect 105. The tissue resection device of aspect 104, wherein the first and second ligating elements comprise a first and second ligating electrode configured for the delivery of radiofrequency energy.

Aspect 106. The tissue resection device of aspect 104, wherein second cutting element is configured to transect tissue between the first and second ligating elements.

Aspect 107. The tissue resection device of aspect 82, further comprising a snare element.

Aspect 108. The tissue resection device of aspect 107, wherein the snare element comprises a flexible line configured for the ligation of tissue.

Aspect 109. The tissue resection device of aspect 107, wherein the snare element comprises a flexible line configured for the transection of tissue.

Aspect 110. The tissue resection device of aspect 107, further comprising a circumferential grooved pathway, said snare element being disposed in the circumferential grooved pathway.

Aspect 111. A tissue resection device configured for coring tissue, the device comprising: a first clamping element comprising a helical coil and a first electrode; and a second clamping element comprising a second electrode, the second clamping element being positioned to oppose at least a portion of the first clamping element, wherein the first and second clamping elements are configured for: (a) the delivery of radiofrequency energy for sealing tissue, and (b) the application of mechanical compression for the transection of tissue.

Aspect 112. The tissue resection device of aspect 111, further comprising an actuator operable to actuate the first or second clamping element to apply mechanical compression to tissue.

Aspect 113. The tissue resection device of aspect 111, wherein the helical coil includes first and second contiguous coil segments.

Aspect 114. The tissue resection device of aspect 113, wherein the first coil segment comprises a generally planar open ring.

Aspect 115. The tissue resection device of aspect 114, wherein the first coil segment is helical and has a pitch of zero.

Aspect 116. The tissue resection device of aspect 113, wherein the second coil segment is helical and has a non-zero pitch.

Aspect 117. The tissue resection device of aspect 116, wherein the second coil segment has a variable pitch.

Aspect 118. The tissue resection device of aspect 113, wherein the first coil segment is helical and has a first pitch and the second coil segment is helical and has a second pitch, and at least one of the first and second pitches is variable.

Aspect 119. The tissue resection device of aspect 111, wherein the first electrode is provided by at least a portion of the helical coil.

Aspect 120. The tissue resection device of aspect 111, wherein the helical coil includes a blunt tip.

Aspect 121. The tissue resection device of aspect 111, wherein the first and second clamping elements have surface profiles that are substantially matching.

Aspect 122. The tissue resection device of aspect 111, further comprising a cutting element.

Aspect 123. The tissue resection device of aspect 122, wherein at least a portion of the cutting element comprises a sharpened edge.

Aspect 124. The tissue resection device of aspect 122, wherein the cutting element comprises at least one electrode configured for the delivery of radiofrequency energy.

Aspect 125. The tissue resection device of aspect 122, wherein the cutting element comprises an ultrasonic blade.

Aspect 126. The tissue resection device of aspect 122, further comprising a second cutting element configured for the amputation the core of tissue from the target tissue site.

Aspect 127. The tissue resection device of aspect 126, wherein at least a portion of the second cutting element comprises a sharpened edge.

Aspect 128. The tissue resection device of aspect 126, wherein the second cutting element comprises at least one electrode configured for the delivery of radiofrequency energy.

Aspect 129. The tissue resection device of aspect 126, wherein the second cutting element comprises an energized wire.

Aspect 130. The tissue resection device of aspect 126, further comprising an actuator operable to actuate the second cutting element to transect tissue.

Aspect 131. A tissue sealing mechanism, the mechanism comprising: a helical coil with a generally obround cross section and a tapered point disposed at a distal end; a first and second helical tissue sealing surface, wherein the first and second helical tissue sealing surfaces are provided by the parallel planar surfaces of the helical coil; a first electrode disposed on the first helical tissue sealing surface; and a second electrode disposed on the second helical tissue sealing surface, wherein the first and second electrodes are configured to apply bipolar radiofrequency energy for sealing tissue.

Aspect 132. The tissue sealing mechanism of aspect 131, wherein the helical coil includes first and second contiguous coil segments.

Aspect 133. The tissue sealing mechanism of aspect 131, wherein the helical coil includes a blunt tip.

Aspect 134. The tissue sealing mechanism of aspect 131, wherein the first and second electrodes have surface profiles that are substantially matching.

Aspect 135. The tissue sealing mechanism of aspect 131, wherein the first and second helical tissue sealing surfaces further comprise a plurality of electrodes configured for the delivery of bipolar radiofrequency energy.

Although shown and described is what is believed to be the most practical and preferred embodiments, it is apparent that departures from specific designs and methods described and shown will suggest themselves to those skilled in the art and may be used without departing from the spirit and scope of the invention. For example, the systems, devices and methods described herein for removal of lesions from the lung. It will be appreciated by the skilled artisan that the devices and methods described herein may are not limited to the lung and could be used for tissue resection and lesion removal in other areas of the body. The present invention is not restricted to the particular constructions described and illustrated, but should be constructed to cohere with all modifications that may fall within the scope of the appended claims.

What is claimed is:

1. A method for coring tissue, the method comprising: disposing a tissue resection device near a target tissue site; rotating a helical coil of the tissue resection device distally through tissue towards the target tissue site; clamping a portion of tissue between a first electrode of a first clamping element and a second electrode of a second clamping element of the tissue resection device, the second electrode being arranged proximal to the first electrode and configured to advance toward the first electrode to clamp the portion of tissue; sealing the portion of tissue clamped between the first electrode and the second electrode by energizing at least one of the first electrode or the second electrode; advancing a cutting element slidably disposed within the second clamping element of the tissue resection device to cut the portion of tissue to form a section of cored tissue; repeating the rotating, the clamping, the sealing, and the advancing steps until the cored tissue is a predetermined size; and removing, after the cored tissue is the predetermined size, the cored tissue from the body, wherein the removing the cored tissue from the body creates a cored cavity at the target tissue site.

2. The method of claim 1, wherein the cored tissue comprises at least a portion of a tissue lesion.

3. The method of claim 1, further comprising disposing a sleeve to provide access to the target tissue site.

4. The method of claim 3, wherein the sleeve comprises a deployable trocar.

5. The method of claim 3, wherein the sleeve comprises electrodes that are configured to seal or ablate adjacent the target tissue site.

6. The method of claim 1, further comprising delivering at least one of radiofrequency energy, chemotherapy, microwave energy, thermal energy, or ultrasonic energy to at least a portion of a wall defining the cored cavity.

7. The method of claim 1, further comprising:
activating, after the cored tissue is the predetermined size, a snare element to sever the cored tissue such that the cored tissue can be removed from the body.

8. The method of claim 7, wherein the activating the snare element includes:
mechanically transecting the cored tissue with the snare element.

9. The method of claim 1, wherein the sealing is effected using radiofrequency energy.

10. The method of claim 1, further comprising:
disposing, after removing the cored tissue, a fill material into the cored cavity such that at least a portion of the cored cavity is sealed.

11. The method of claim 1, wherein the first electrode is disposed on a proximal surface of the helical coil.

12. The method of claim 11, wherein the clamping the portion of tissue between the first electrode and the second electrode includes:
causing the second electrode to close against the helical coil.

13. The method of claim 1, wherein the clamping the portion of tissue occurs after the rotating the helical coil, the sealing the portion of tissue occurs after the clamping the portion of tissue, and the advancing the cutting element occurs after the sealing the portion of tissue.

14. A method for coring tissue, the method comprising: disposing a tissue resection device near a target tissue site; rotating a helical coil coupled to a first tube of the tissue resection device distally through tissue towards the target tissue site; advancing a distal edge of a second tube of the tissue resection device towards the target tissue site such that a portion of tissue is clamped between a first electrode disposed on a proximal surface of the helical coil and a second electrode disposed on the distal edge of the second tube of the tissue resection device; and energizing at least one of the first electrode or the second electrode with radiofrequency energy; advancing a cutting element disposed within the second tube of the tissue resection device to cut the portion of tissue to form a section of cored tissue.

15. The method of claim 14, further comprising:
rotating, after the advancing the cutting element, the helical coil further towards the target tissue site.

16. The method of claim 14, further comprising repeating the rotating, the clamping, the energizing, and the advancing a cutting element steps a plurality of times until the cored tissue is a predetermined size.

17. The method of claim 16, further comprising:
activating, after the cored tissue is the predetermined size, a snare element to sever the cored tissue such that the cored tissue can be removed from a body of a patient.

18. The method of claim 16, further comprising:
anchoring to the target tissue site prior to rotating the helical coil, wherein the cored tissue includes the anchored target tissue site.

19. The method of claim 14, further including:
sensing a presence of tissue at an end effector, the end effector including the first electrode and the second electrode; and
energizing, when the presence of tissue is detected, at least one of the first electrode or the second electrode with radiofrequency energy.

20. The method of claim 14, wherein the energizing at least one of the first electrode or the second electrode with radiofrequency energy includes:
sealing blood vessels in the portion of tissue clamped between the first electrode and the second electrode.

21. The method of claim 14, wherein the first tube is an outer tube, the second tube is a central tube slidably disposed in the outer tube.

22. The method of claim 14, wherein the first electrode is disposed on a planar portion of the helical coil such that a surface profile of the first electrode and a surface profile of the second electrode are substantially matching.

23. A method for coring tissue, the method comprising: disposing a tissue resection device near a target tissue site; rotating a helical coil of the tissue resection device distally through tissue towards the target tissue site; clamping, after rotating the helical coil, a portion of tissue between a first electrode and a second electrode of the tissue resection device by advancing the second electrode distally toward the first electrode to clamp the portion of tissue between the first electrode and the second electrode, the second electrode being disposed on a distal edge of a tube; sealing, after the clamping, the portion of tissue clamped between the first electrode and the second electrode by energizing at least one of the first electrode or the second electrode with radiofrequency energy; and advancing, after the sealing, a cutting element slidably disposed in the tube of the tissue resection device to cut sealed tissue to form a section of cored tissue.

24. The method of claim 23, wherein the first electrode is disposed on a proximal surface of the helical coil and the second electrode is arranged proximal to the first electrode.

25. The method of claim 24, wherein the first electrode is disposed on a planar surface of the helical coil such that a surface profile of the first electrode and a surface profile of the second electrode are substantially matching.

26. The method of claim 24, wherein the clamping the portion of tissue between the first electrode and the second electrode includes causing the second electrode to close against the helical coil.

27. The method of claim 24, wherein the tube is a central tube, the helical coil is coupled to an outer tube, and the central tube is slidably disposed in the outer tube.

28. The method of claim 23, further comprising:

repeating the rotating, the clamping, the sealing, and the advancing steps to form the cored tissue until the cored tissue is a predetermined size.

29. The method of claim 28, further comprising: anchoring an anchor device to the target tissue site prior to rotating the helical coil.

30. The method of claim 28, further comprising:

activating, after the cored tissue is the predetermined size, a snare element to pull and sever the cored tissue.

31. The method of claim 30, further comprising:

removing, after activating the snare element to sever the cored tissue, the cored tissue from a body of a patient to create a cored cavity at the target tissue site; and disposing a fill material into the cored cavity such that at least a portion of the cored cavity is sealed.

\* \* \* \* \*